United States Patent
Kemp et al.

(10) Patent No.: US 10,456,525 B2
(45) Date of Patent: Oct. 29, 2019

(54) DETENT MECHANISM FOR A MEDICAMENT DELIVERY DEVICE

(71) Applicant: SANOFI-AVENTIS DEUTSCHLAND GMBH, Frankfurt am Main (DE)

(72) Inventors: Thomas Kemp, Hertfordshire (GB); Simon Brereton, Cambridgeshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 609 days.

(21) Appl. No.: 14/395,997

(22) PCT Filed: May 3, 2013

(86) PCT No.: PCT/EP2013/059282
§ 371 (c)(1),
(2) Date: Oct. 21, 2014

(87) PCT Pub. No.: WO2013/167494
PCT Pub. Date: Nov. 14, 2013

(65) Prior Publication Data
US 2015/0088077 A1    Mar. 26, 2015

(30) Foreign Application Priority Data

May 7, 2012 (EP) ................................... 12166990

(51) Int. Cl.
*A61M 5/20* (2006.01)
(52) U.S. Cl.
CPC ..... *A61M 5/2033* (2013.01); *A61M 2005/206* (2013.01); *A61M 2005/208* (2013.01); *A61M 2005/2013* (2013.01)

(58) Field of Classification Search
CPC .......... A61M 5/2033; A61M 2005/206; A61M 5/3272; A61M 2005/2073;
(Continued)

(56) References Cited

U.S. PATENT DOCUMENTS

| 5,188,598 | A | 2/1993 | Thead et al. |
| 2005/0027255 | A1* | 2/2005 | Lavi .................... A61M 5/2033 |
| | | | 604/135 |

(Continued)

FOREIGN PATENT DOCUMENTS

| CN | 103492002 | 1/2014 |
| EP | 2399630 | 12/2011 |

(Continued)

OTHER PUBLICATIONS

Chinese Search Report in Chinese Application No. 201380022204.9, dated May 3, 2013, 2 pages.

(Continued)

*Primary Examiner* — Kami A Bosworth
*Assistant Examiner* — Alexandra Lalonde
(74) *Attorney, Agent, or Firm* — Fish & Richardson P.C.

(57) ABSTRACT

Described is an auto-injector comprising a syringe carrier adapted to contain a syringe. The syringe carrier has a ramp member with a first ramp and a second ramp. The auto-injector comprises a chassis including a resilient beam having a beam head adapted to engage the ramp member. The first ramp is adapted to deflect the beam head in a radial direction relative to the chassis and the second ramp is adapted to deflect the beam head in a tangential direction relative to the chassis.

14 Claims, 26 Drawing Sheets

(58) Field of Classification Search
CPC .... A61M 2005/208; A61M 2005/2013; A61M 5/3271
See application file for complete search history.

(56) References Cited

U.S. PATENT DOCUMENTS

| | | | |
|---|---|---|---|
| 2006/0189933 A1* | 8/2006 | Alheidt | A61M 5/326 604/110 |
| 2008/0009807 A1 | 1/2008 | Hommann | |
| 2012/0116319 A1* | 5/2012 | Grunhut | A61M 5/2033 604/198 |
| 2013/0079718 A1* | 3/2013 | Shang | A61M 5/20 604/131 |

FOREIGN PATENT DOCUMENTS

| | | |
|---|---|---|
| EP | 2489390 | 8/2012 |
| JP | H05/253300 | 5/1993 |
| JP | 2003/534105 | 11/2003 |
| JP | 2005/152541 | 6/2005 |
| MX | 2013009165 | 8/2013 |
| RU | 2203688 | 5/2003 |
| WO | WO 01/91837 | 12/2001 |
| WO | WO 2010/113388 | 10/2010 |
| WO | 2011/012849 | 2/2011 |
| WO | WO 2011012849 A1 * | 2/2011 .......... A61M 5/2033 |
| WO | WO 2012/000873 | 1/2012 |
| WO | 2012/045833 | 4/2012 |
| WO | WO 2012045833 A1 * | 4/2012 .......... A61M 5/2033 |
| WO | WO 2012/110580 | 8/2012 |

OTHER PUBLICATIONS

European Search Report in European Application No. 12166990.7, dated Sep. 19, 2012, 6 pages.
International Preliminary Report on Patentability in International Application No. PCT/EP2013/059282, dated Nov. 11, 2014, 7 pages.
International Search Report for Int. App. No. PCT/EP2013/059282, dated Jul. 23, 2013.
Japanese Office Action in Application No. 2015-545750, dated Oct. 3, 2017, 3 pages.
Mexican Office Action in Application No. MX/a/2014/013636, dated Jun. 20, 2013, 5 pages.
Russian Search Report in Application No. 2014149220, dated Mar. 5, 2017.

* cited by examiner

DETENT MECHANISM FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2013/059282 filed May 3, 2013, which claims priority to European Patent Application No. 12166990.7 filed on May 7, 2012. The entire disclosure contents of these applications are herewith incorporated by reference into the present application.

BACKGROUND

Detent mechanisms are applied to control motion of components relative to each other in a manner keeping them in a defined relative position until a predetermined force is overcome suddenly allowing one of the components to move relative to the other, wherein the subsequent motion can be achieved by application of a significantly reduced force. The motion may end at another relative position defined by the detent mechanism in such a manner that a predetermined force has to be overcome to move the component back into its initial position.

Detent mechanisms are conventionally used in medicament delivery devices to control relative movement of components. For example, a detent mechanism may be used to control axial movement of a syringe relative to the delivery device to ensure that needle penetration depth is appropriate. However, given certain constraints associated with the design of medicament delivery devices (e.g., preventing component failure, ensuring safety, ensuring appropriate needle penetration depth, ensuring full delivery of medicament, etc.), there remains a need for an improved detent mechanism for a medicament delivery device.

SUMMARY

One possible object of the present invention to provide a detent mechanism for a medicament delivery device.

In an exemplary embodiment, an auto-injector according to the present invention comprises a syringe carrier adapted to contain a syringe. The syringe carrier has a ramp member with a first ramp and a second ramp. The auto-injector comprises a chassis including a resilient beam having a beam head adapted to engage the ramp member. The first ramp is adapted to deflect the beam head in a radial direction relative to the chassis and the second ramp is adapted to deflect the beam head in a tangential direction relative to the chassis.

In an exemplary embodiment, the beam head is deflected by the first ramp when the syringe carrier moves in a first direction relative to the chassis, and the beam head is deflected by the second ramp when the syringe carrier moves in a second direction relative to the chassis.

In an exemplary embodiment, the auto-injector further comprises a case including a first rib and a resilient element, both adapted to engage the beam head. The beam head includes a first beam head adapted to engage the ramp member and a second beam head adapted to engage the case. The first beam head has a contoured engagement surface.

In an exemplary embodiment, the first ramp is formed on a proximal portion of the ramp member and the second ramp is formed on a distal portion of the ramp member.

In an exemplary embodiment, in a first state, the beam head abuts the first rib and the first ramp to prevent movement of the syringe carrier relative to the chassis. In a second state, the beam head is deflected radially by the first ramp and causes the resilient element to deflect radially. In a third state, the beam head disengages the first ramp and the syringe carrier is translatable relative to the chassis. In the third state, the beam head remains in contact with the ramp member. In a fourth state, the beam head is in a non-deflected position distal of the second ramp. The beam head reaches the fourth state when the syringe carrier translates in the first direction relative to the chassis a predetermined distance at least equal to a length of the ramp member. In a fifth state, the beam head is deflected tangentially by the second ramp and the syringe carrier is translatable relative to the chassis. The beam head reaches the fifth state when the syringe carrier translates in the second direction relative to the chassis until the beam head abuts the second ramp.

In an exemplary embodiment, a first plane of the first ramp intersects a second plane of the second ramp at a non-perpendicular angle.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-

N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and 6 approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
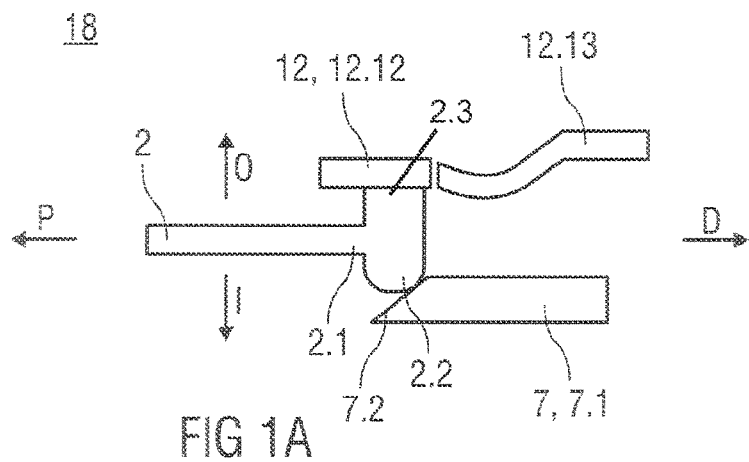
FIG. 1A is a schematic lateral view of an exemplary embodiment of a detent mechanism in a first state A.
Figure 1B:
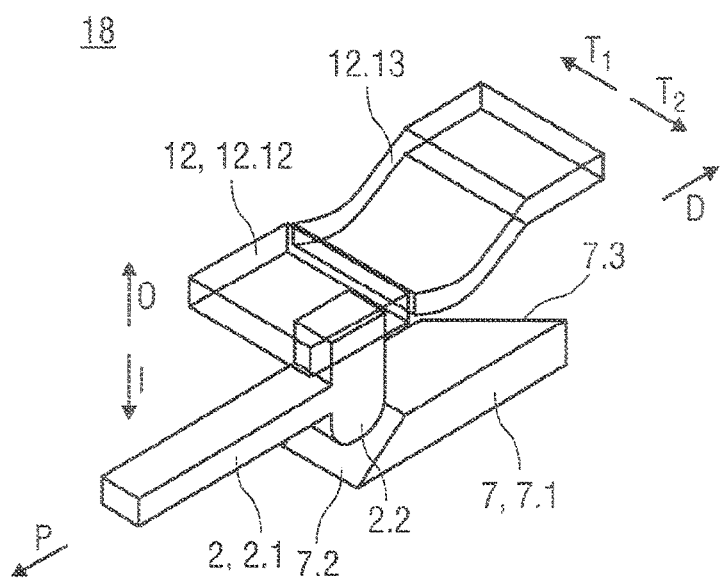
FIG. 1B is a perspective view of the detent mechanism in state A.

FIG. 1A is a schematic lateral view of an exemplary embodiment of a detent mechanism 18 in a first state A; FIG. 1B shows a respective perspective view of the detent mechanism 18 in the first state A. The detent mechanism 18 controls translation of a first component 2 relative to a second component 7 in a longitudinal direction, e.g. a proximal direction P or a distal direction D. In an exemplary embodiment of a medicament delivery device (e.g., an autoinjector), the first component 2 may be a chassis 2 and the second component 7 may be a syringe carrier 7 (both shown in, e.g., FIGS. 6A and 6B), each of which are housed within and translatable relative to a case 12. Those of skill in the art will understand that the description of the detent mechanism 18 need not be implemented in the exact manner described; for example, the first component may be the syringe carrier 7 and the second component may be the chassis 2. Further, while the exemplary embodiment of the detent mechanism 18 will be described with reference to an autoinjector, those of skill in the art will understand that the detent mechanism 18 may be utilized in other medicament delivery devices including, but not limited to, pen injectors, safety syringes, safety needles, infusion systems, etc.

Referring back to FIGS. 1A and 1B, in an exemplary embodiment, the chassis 2 includes a resilient beam having a beam head 2.1 with a first beam head 2.2 which is adapted to engage a ramp member 7.1 on the carrier 7 and a second beam head 2.3 which is adapted to abut a first rib 12.12 on the case 12. The ramp member 7.1 includes a radial ramp 7.2 and a tangential ramp 7.3. The radial ramp 7.2 may incline radially from the proximal direction P to the distal direction D, and the tangential ramp 7.3 may incline tangentially from a first tangential direction $T_1$ to a second tangential direction $T_2$, as shown in FIG. 1B.

In state A, the first beam head 2.2 abuts the radial ramp 7.2. In an exemplary embodiment, the first beam head 2.2 has a contoured engagement surface which abuts the radial ramp 7.2 and provides a resistive force when the carrier 7 attempts to move in the proximal direction P relative to the chassis 2. In state A, the first rib 12.12 abuts the second beam head 2.3, which prevents radial movement of the beam head 2.1 and, thus, prevents movement of the carrier 7 in the proximal direction P relative to the chassis 2.

Figure 2A:
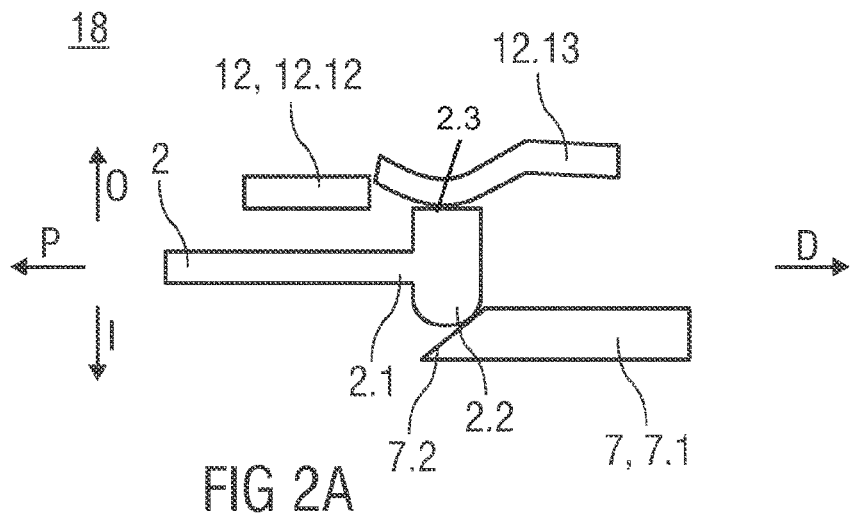
FIG. 2A is a schematic lateral view of the detent mechanism in a second state B.
Figure 2B:
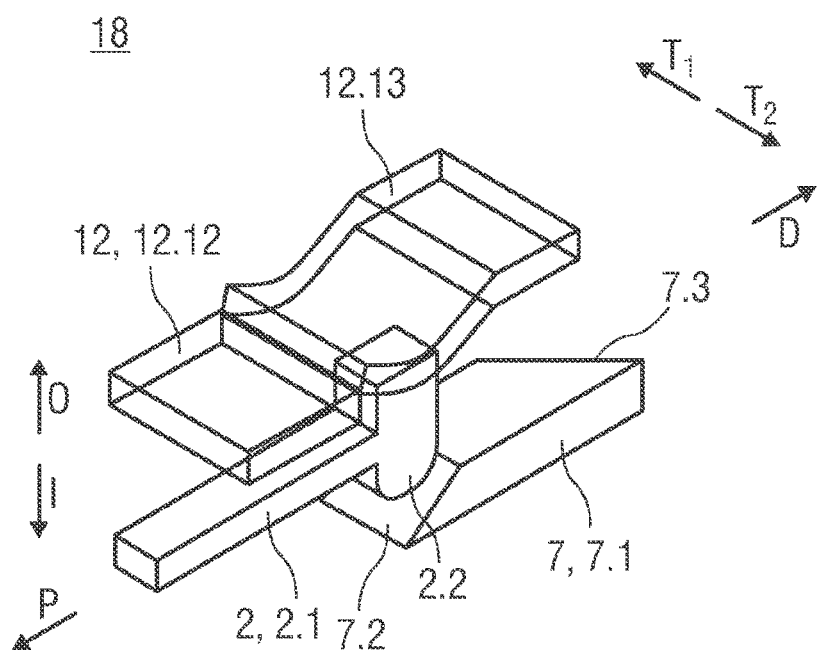
FIG. 2B is a perspective view of the detent mechanism in state B.

FIG. 2A is a schematic lateral view of the detent mechanism 18 in a second state B; FIG. 2B shows a respective perspective view of the detent mechanism 18 in state B. In state B, the case 12 moves in the proximal direction P relative to the chassis 2 and the carrier 7. As the case 12 moves in the proximal direction P, the second beam head 2.3 engages a resilient element 12.13 on the case 12, causing the resilient element 12.13 to deflect radially.

Figure 3A:
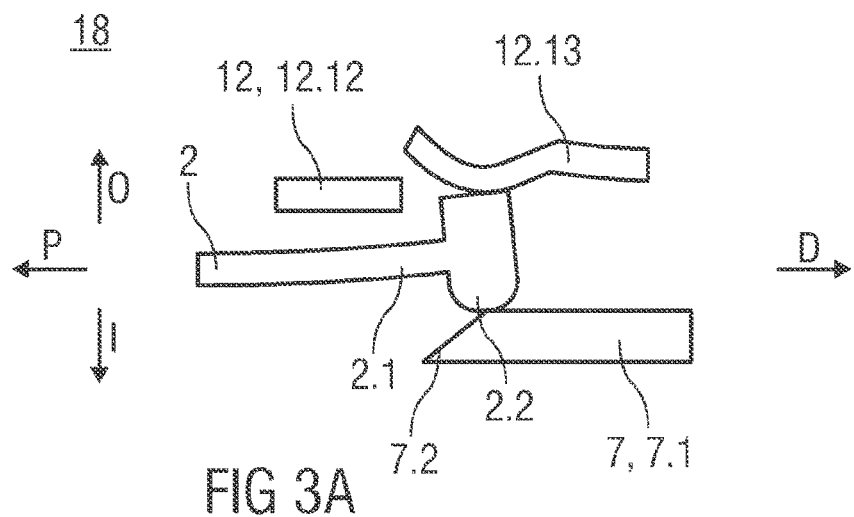
FIG. 3A is a schematic lateral view of the detent mechanism in a third state C.
Figure 3B:
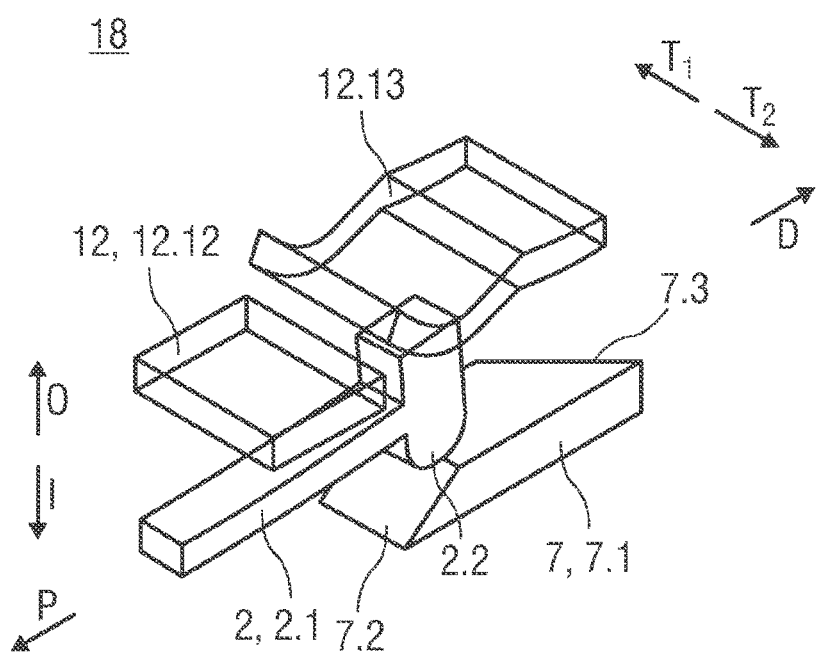
FIG. 3B is a perspective view of the detent mechanism in state C.

FIG. 3A is a schematic lateral view of the detent mechanism 18 in a third state C; FIG. 3B shows a respective perspective view of the detent mechanism 18 in state C. When a proximally directed force is applied to the carrier 7 and overcomes a radial force provided by the resilient element 12.13 and a resilient force of the beam head 2.1, the radial ramp 7.2 causes the beam head 2.1 to deflect radially and the carrier 7 translates in the proximal direction P relative to the chassis 2 and the case 12.

Figure 4A:
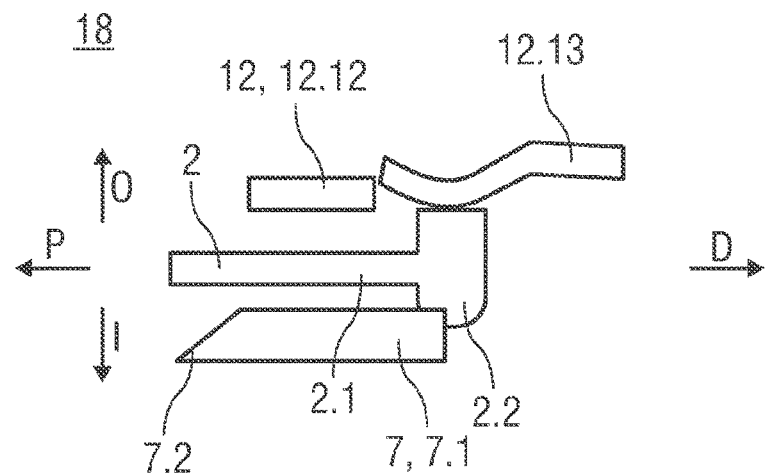
FIG. 4A is a schematic lateral view of the detent mechanism in a fourth state D.
Figure 4B:
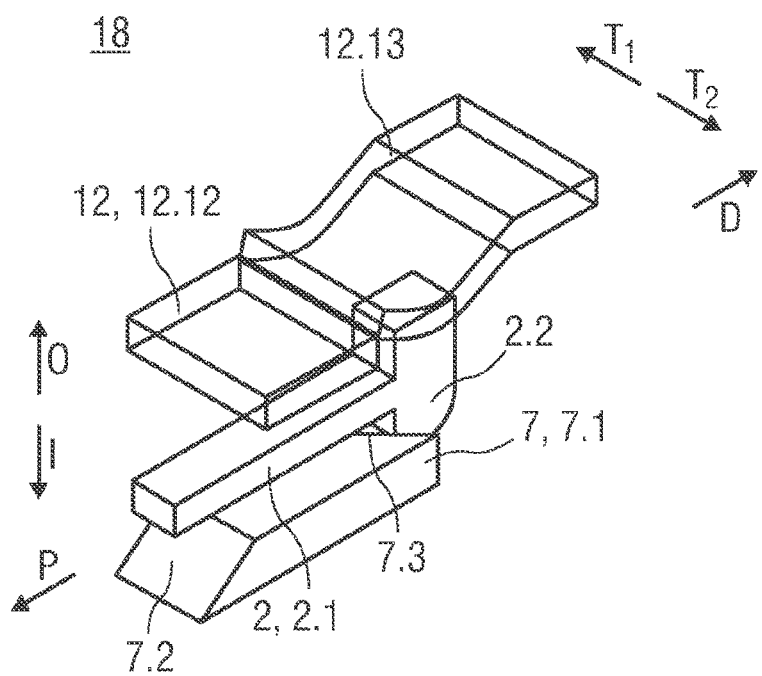
FIG. 4B is a perspective view of the detent mechanism in state D.

FIG. 4A is a schematic lateral view of the detent mechanism 18 in a fourth state D; FIG. 4B shows a respective perspective view of the detent mechanism 18 in state D. When the carrier 7 moves in the proximal direction P a sufficient distance relative to the chassis 2 and the case 12, the radial force provided by the resilient element 12.13 and the resilient force in the beam causes the beam head 2.1 to return to an axial, non-deflected position distal of the tangential ramp 7.3.

Figure 5A:
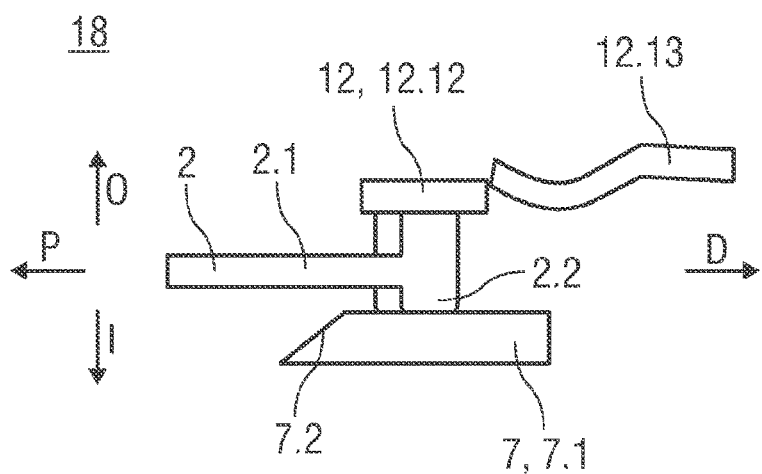
FIG. 5A is a schematic lateral view of the detent mechanism in a fifth state E.
Figure 5B:
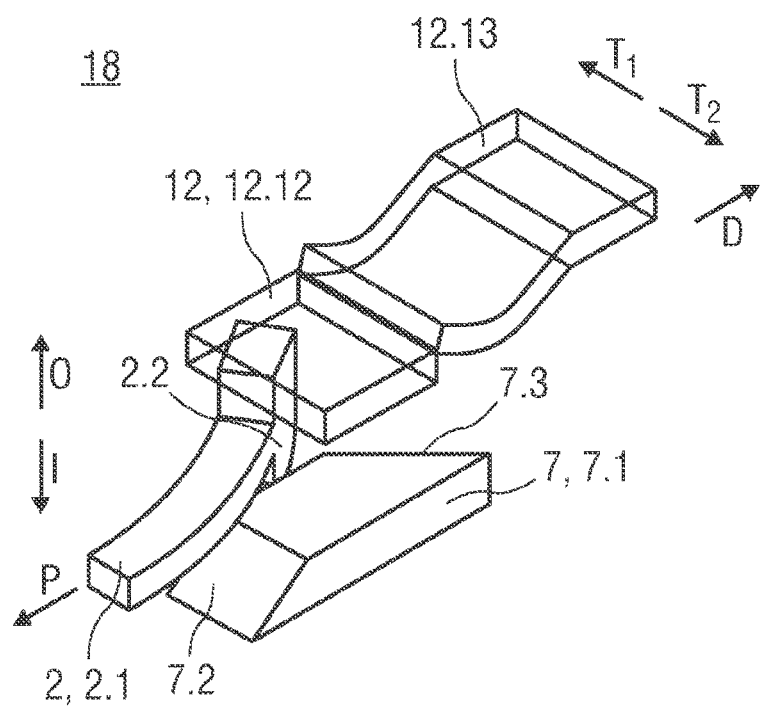
FIG. 5B is a perspective view of the detent mechanism in state E.

FIG. 5A is a schematic lateral view of the detent mechanism 18 in a fifth state E; FIG. 5B shows a respective perspective view of the detent mechanism 18 in state E. When the carrier 7 and the case 12 move in the distal direction D relative to the chassis 2, the tangential ramp 7.3 causes the beam head 2.1 to deflect tangentially. Deflection of the beam head 2.1 requires a force which may decrease speed of relative movement of the carrier 7 and the chassis 2. When the carrier 7 has moved a sufficient distance in the distal direction D relative to the chassis 2 and the case 12, the beam head 2.1 returns to its axial, non-deflected position in state A. Because the resilient element 12.13 has returned to is non-deflected position and the first rib 12.12 has returned to its original position relative to the carrier 7 (as shown in state A), the carrier 7 cannot move in the proximal direction P relative to the chassis 2 (or vice-versa). The beam head 2.1 is prevented from radial movement, because it abuts the first rib 12.12 and therefore cannot pass over the radial ramp 7.2.

In a more general embodiment, the radial ramp 7.2 and the tangential ramp 7.3 could be arranged to deflect the beam head 2.1 in two different directions which do not necessarily have to be oriented at 90° relative to each other. Consequentially, the deflection caused by the radial ramp 7.2 does not necessarily have to be directed in a direction that is perpendicular to deflection caused by the tangential ramp 7.3, and the opposing directions of deflection, in some exemplary embodiments, may not be 180°. Those of skill in the art will understand that the detent beam 2.1 may likewise be part of the second component 7 and the ramp member 7.1 may be part of the first component 2.

Figure 6A:
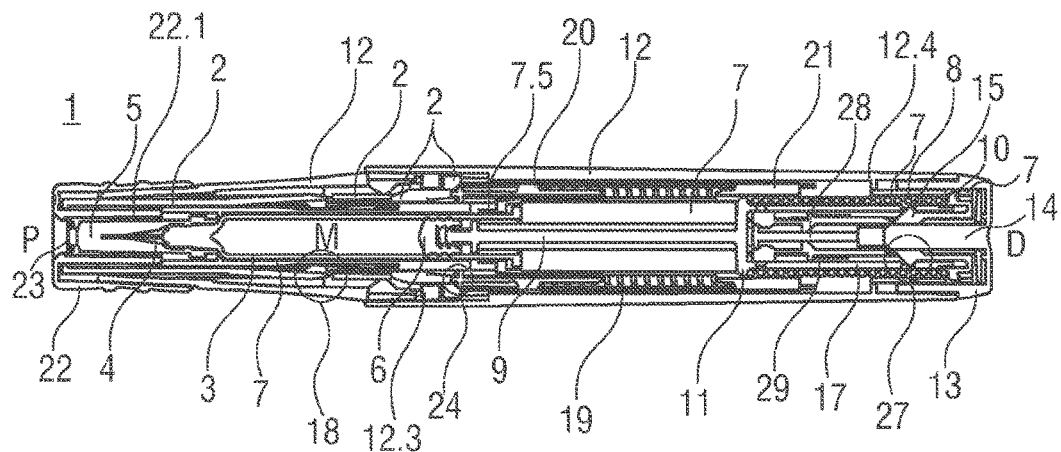
FIG. 6 shows two longitudinal sections of an exemplary embodiment of an auto-injector in different section planes in a state prior to use.
Figure 6B:
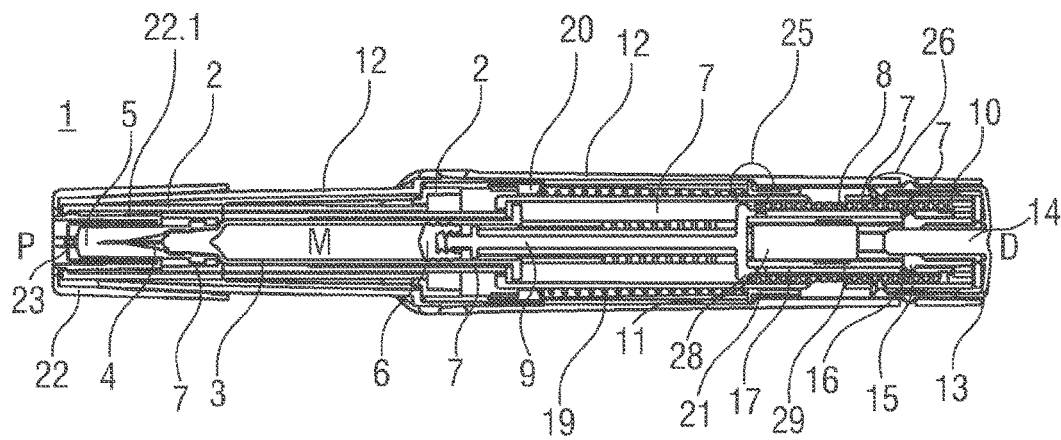

FIGS. 6a and 6b show two longitudinal sections of an exemplary embodiment of a medicament delivery device, e.g., an auto-injector 1, incorporating a detent mechanism according to the present invention. FIGS. 6a and 6b show two longitudinal sections in different section planes, the different section planes approximately 90° rotated to each other, wherein the auto-injector 1 is in an initial state prior to starting an injection. The auto-injector 1 comprises a chassis 2. In the following description, the chassis 2 is generally considered as being fixed in position so motion of other components is described relative to the chassis 2. A syringe 3, e.g. a Hypak syringe, with a hollow injection needle 4 is arranged in a proximal part of the auto-injector 1. When the auto-injector 1 or the syringe 3 is assembled a protective needle sheath 5 is attached to the needle 4. A stopper 6 is arranged for sealing the syringe 3 distally and for displacing a liquid medicament M through the hollow needle 4. The syringe 3 is held in a carrier 7 and supported at its proximal end therein. The carrier 7 is slidably arranged in the chassis 2.

A drive spring 8, e.g., a compression spring, is arranged in a distal part of the carrier 7. A plunger 9 serves for forwarding the force of the drive spring 8 to the stopper 6.

The drive spring 8 is loaded between a distal carrier end face 10 of the carrier 7 and a thrust face 11 arranged distally on the plunger 9.

The carrier 7, the drive spring 8 and the plunger 9 work together to eject the medicament M from the syringe 3. These components can therefore be referred to as a drive sub-assembly.

Figure 19A:
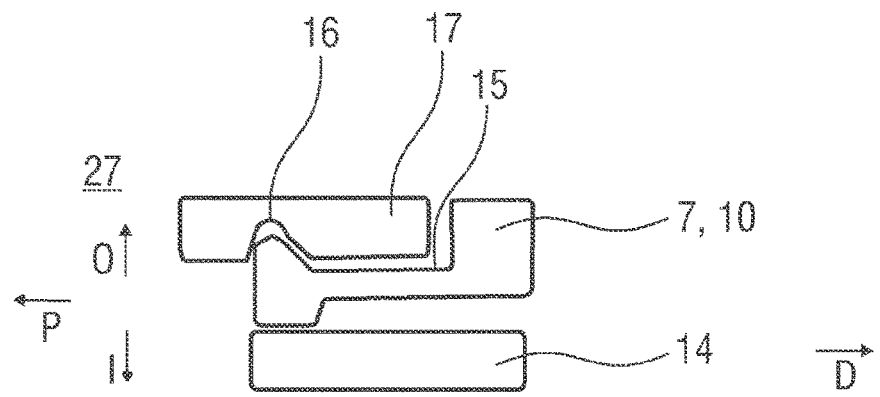
FIG. 19 shows schematic views of an exemplary embodiment of a plunger release mechanism in three different states.

The chassis 2 and the carrier 7 are arranged within a case 12. In an exemplary embodiment, a trigger button 13 is arranged at a distal end of the case 12. In an exemplary plunger release mechanism 27, a peg 14 protrudes from a distal end face of the trigger button 13 in the proximal direction P between two resilient arms 15 originating from the distal carrier end face 10 of the carrier 7 thus preventing the arms 15 from flexing towards each other in an initial state A illustrated in FIG. 19A. In FIG. 19A, only one of the resilient arms 15 is shown to illustrate the principle. Outwardly the resilient arms 15 are caught in respective first recesses 16 in a distal plunger sleeve 17 attached distally to the thrust face 11 and arranged inside the drive spring 8. The engagement of the resilient arms 15 in the first recesses 16 prevents axial translation of the plunger 9 relative to the carrier 7. The resilient arms 15 are ramped in a manner to flex them inwards on relative motion between the plunger 9 and the carrier 7 under load of the drive spring 8, which is prevented by the peg 14 in the initial state A.

When the auto-injector 1 is in its initial state, the carrier 7 is locked to the chassis 2 by the detent mechanism 18 as shown in FIGS. 1A and 1B.

Figure 20A:
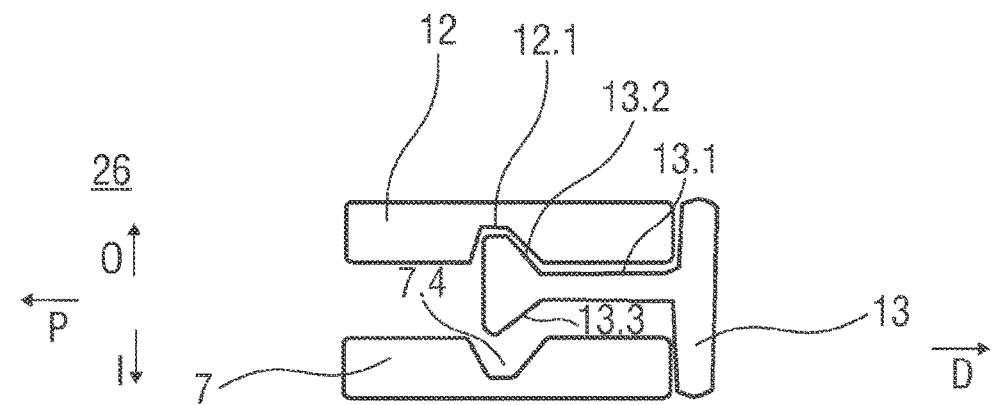
FIG. 20 shows schematic views of an exemplary embodiment of a button release mechanism in three different states.
Figure 20B:
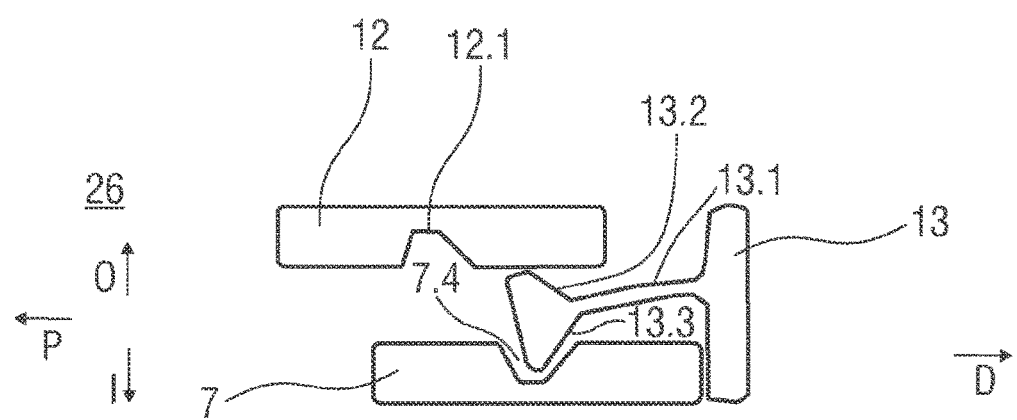

The trigger button 13 is initially engaged to the case 12 by a button release mechanism 26 and cannot be depressed. The button release mechanism 26 is illustrated in detail in FIGS. 20A to 20C. Referring now to FIG. 20A, the button release mechanism 26 comprises a resilient proximal beam 13.1 on the trigger button 13, the proximal beam 13.1 having an outward fourth ramp 13.2 and an inward fifth ramp 13.3. In an initial state A illustrated in FIG. 20A the outward fourth ramp 13.2 is engaged in a ramped first case detent 12.1 preventing the trigger button 13 from moving out of the distal end D. The trigger button 13 proximally abuts both the case 12 and the carrier 7 hence being prevented from being depressed in the proximal direction P.

Referring again to FIGS. 6A and 6B a control spring 19 in the shape of another compression spring is arranged around the carrier 7 and acts between a proximal first collar 20 and a distal second collar 21. The control spring 19 is used to move the carrier 7 and hence the drive sub-assembly in the proximal direction P for needle insertion or in the distal direction D for needle retraction.

In the state as delivered as shown in FIGS. 6A and 6B a cap 22 is attached to the proximal end of the case 12 and the protective needle sheath 5 is still in place over the needle 4 and the needle hub. An inner sleeve 22.1 of the cap 22 is arranged inside the chassis 2 and over the protective needle sheath 5. In the inner sleeve 22.1 a barb 23 is attached. The barb 23 is engaged to the protective needle sheath 5 for joint axial translation.

Figure 7A:
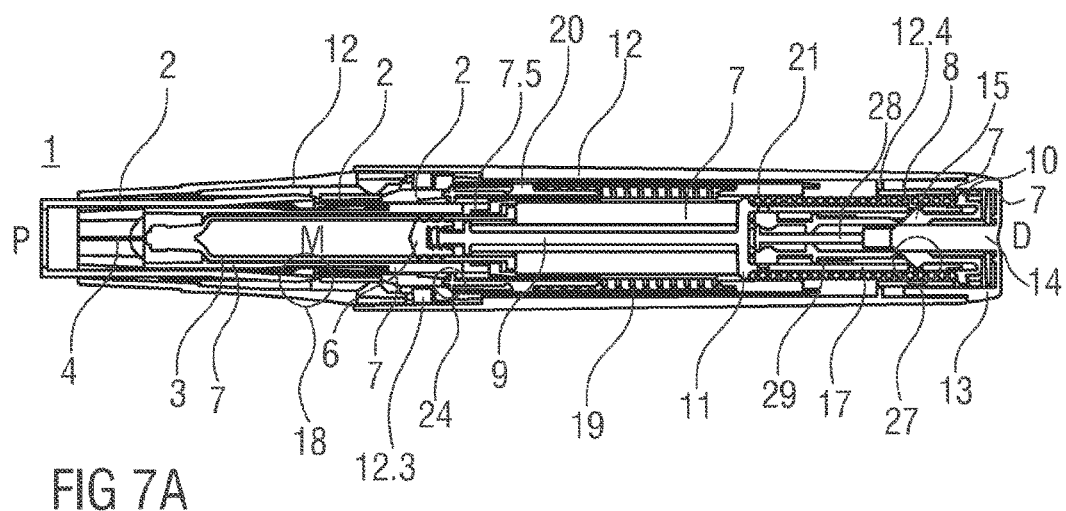
FIG. 7 shows two longitudinal sections of an exemplary embodiment of the auto-injector after removal of a cap and a protective needle sheath.
Figure 7B:
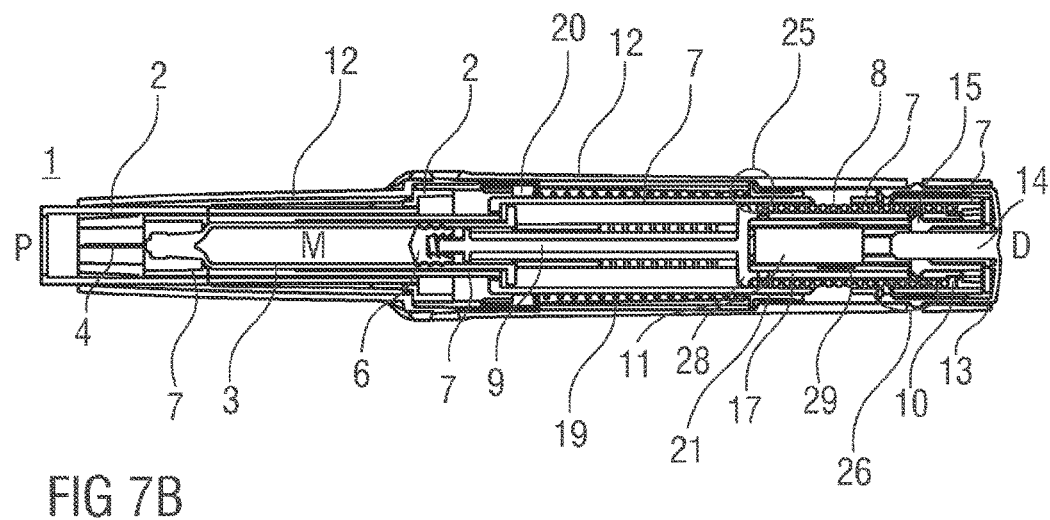

A sequence of operation of the auto-injector 1 is as follows:

A user pulls the cap 22 from the proximal end of the case 12. The barb 23 joins the protective needle sheath 5 to the cap 22. Hence, the protective needle sheath 5 is also removed on removal of the cap 22. FIGS. 7A and 7B show the auto-injector 1 with the cap 22 and needle sheath 5 removed. The carrier 7 with the syringe 3 are prevented from moving in the proximal direction P relative to the chassis 2 by the detent mechanism 18 being in state A as in FIGS. 1A and 1B.

Figure 8A:
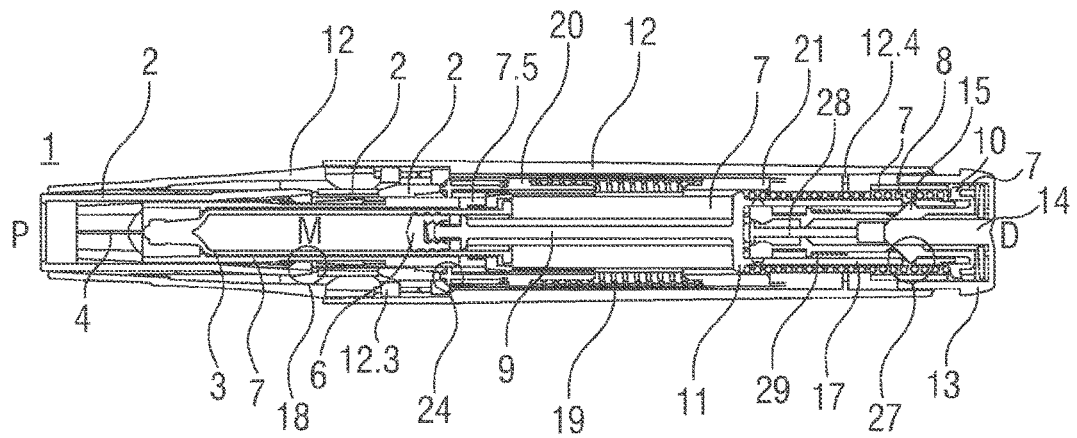
FIG. 8 shows two longitudinal sections of an exemplary embodiment of the auto-injector with a proximal end pressed against an injection site.
Figure 8B:
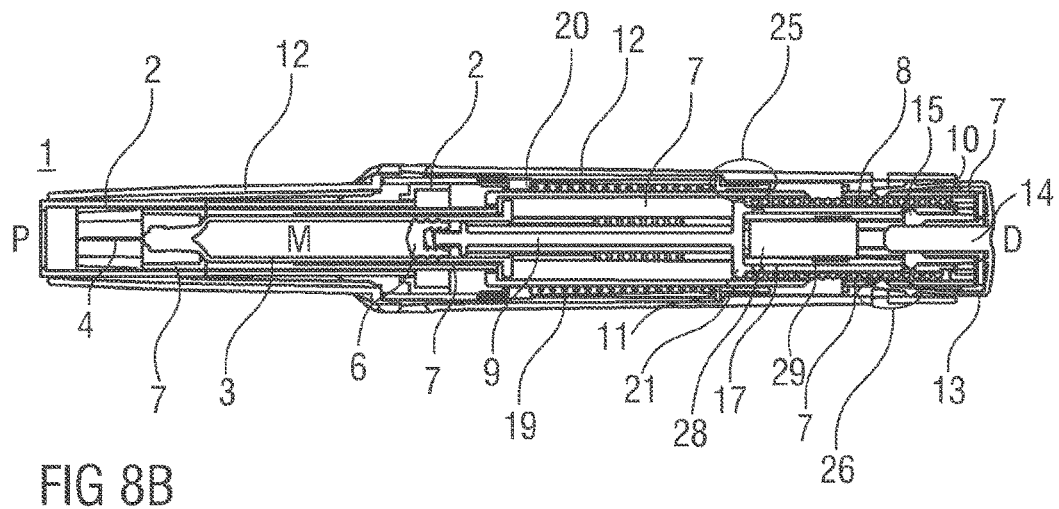
Figure 16A:
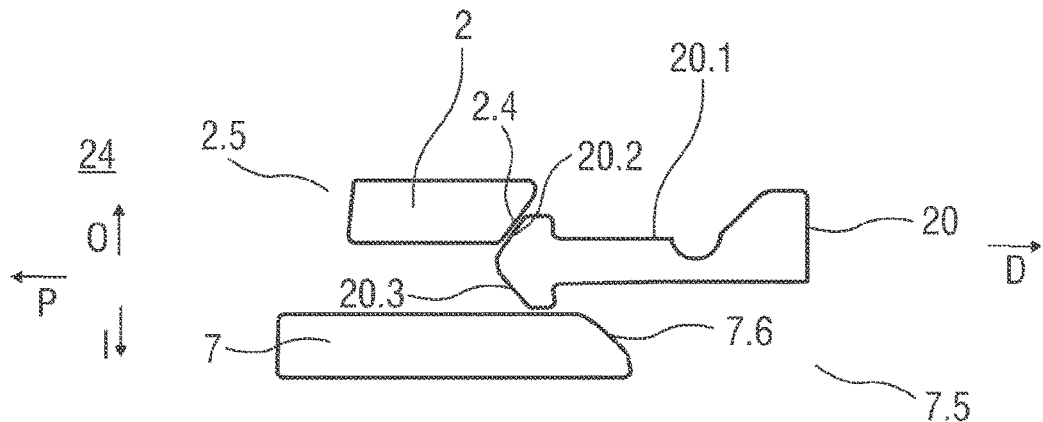
FIG. 16 shows schematic views of a needle insertion control mechanism for controlling movement of a first collar in six different states.

Referring to FIGS. 7A and 7B the user holds the case 12 and places the chassis 2 protruding from the case 12 at the proximal end P against an injection site, e.g. a patient's skin. As the auto-injector 1 is pressed against the injection site, the case 12 translates in the proximal direction P relative to the chassis 2 into an advanced position as illustrated in FIGS. 8A and 8B. The second collar 21 is locked to the case 12 and is moved with the case 12 relative to the chassis 2 and relative to nearly all other components of the auto-injector 1 thus slightly compressing the control spring 19 against the first collar 20 which is prevented from moving in the proximal direction P by the chassis 2 due to a needle insertion control mechanism 24 being in a state A illustrated in detail in FIG. 16A. Referring now to FIG. 16A, a resilient member in the shape of an arrowhead 20.1 is proximally arranged on the first collar 20. The first collar 20 with the arrowhead 20.1 is being forced in the proximal direction P under load of the compressed control spring 19. An outward sixth ramp 20.2 on the arrowhead 20.1 interacts with a second distal seventh ramp 2.4 on the chassis 2 ramping the arrowhead 20.1 in an inward direction I which is prevented by the arrowhead 20.1 inwardly abutting the carrier 7. Hence, the first collar 20 cannot translate in the proximal direction P.

Figure 17A:
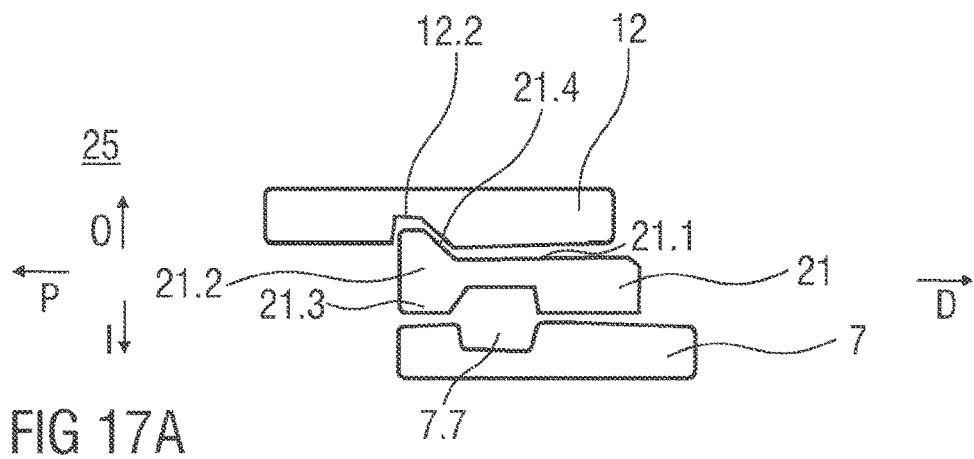
FIG. 17 shows schematic views of an exemplary embodiment of a syringe retraction control mechanism in three different states.

Referring again to FIGS. 8A and 8B the second collar 21 is locked to the case due to a syringe refraction control mechanism 25 being in a state A illustrated in detail in FIG. 17A. Referring now to FIG. 17A, the syringe retraction control mechanism 25 comprises a resilient proximal beam 21.1 on the second collar 21, the proximal beam 21.1 having a second beam head 21.2 having an inward boss 21.3 and a distal outward eighth ramp 21.4. The distal outward eighth ramp 21.4 is engaged in a ramped second case detent 12.2 in a manner ramping the second beam head 21.1 in the inward direction I with the second collar 21 under load of the control spring 19 in the distal direction D which is prevented by the inward boss 21.3 inwardly abutting the carrier 7.

Referring again to FIGS. 8A and 8B, if the user was to move the case 12 away from the injection site, the control spring 19 expands returning the auto-injector 1 to the initial condition after removal of the cap 22 as illustrated in FIGS. 7A and 7B.

In the state as in FIGS. 8A and 8B the carrier 7 continues to be prevented from moving in the proximal direction P by the detent mechanism 18, however with the case 12 in its advanced position the detent mechanism 18 is unlocked as the first rib 12.12 on the case 12 has also moved and no longer prevents outward deflection of the beam head 2.1 (as shown in FIGS. 2A and 2B). Movement of the case 12 relative to the carrier 7, which is locked to the chassis 2 by the detent mechanism 18, causes the button release mechanism 26 to switch to a state B illustrated in FIG. 20B. The trigger button 13 cannot translate with the case 12 in the proximal direction P as it is abutted against the carrier 7. The ramp on the first case detent 12.1 interacts with the outward fourth ramp 13.2 on the proximal beam 13.1 on the trigger button 13 deflecting the proximal beam 13.1 in the inward direction I thus engaging the inward fifth ramp 13.3 on the proximal beam 13.1 in a ramped carrier detent 7.4 arranged in the carrier 7. As the case 12 is translated further in the proximal direction P it supports the proximal beam 13.1 outwardly thus locking the trigger button 13 to the carrier 7. The trigger button 13 now protrudes from the distal end D of the chassis 12 and is ready to be pressed.

In the state as in FIGS. 8A and 8B the user depresses the trigger button 13 in the proximal direction P. As the trigger button 13 abuts against the carrier 7, the carrier 7 is pushed in the proximal direction P against the chassis 2. The detent mechanism 18 provides a resistive force when the user pushes the trigger button 13. Once the user applies a force which exceeds a pre-determined value (e.g., the force required for the beam head 2.1 to deflect radially on the radial ramp 7.2 and deflect the resilient element 12.13 on the case 12 radially), the detent mechanism 18 releases from state B as illustrated in FIGS. 2A and 2B and enters state C as illustrated in FIGS. 3A and 3B, initiating the injection cycle. When the carrier 7 travels sufficiently far in the proximal direction P relative to the chassis 2, the ramp member 7.1 on the carrier 7 passes under the deflected first beam head 2.2 thus allowing it to relax and move back in the radial inward direction I distally behind the ramp member 7.1, abutting the tangential ramp 7.3 in state D illustrated in FIGS. 4A and 4B.

Figure 16B:
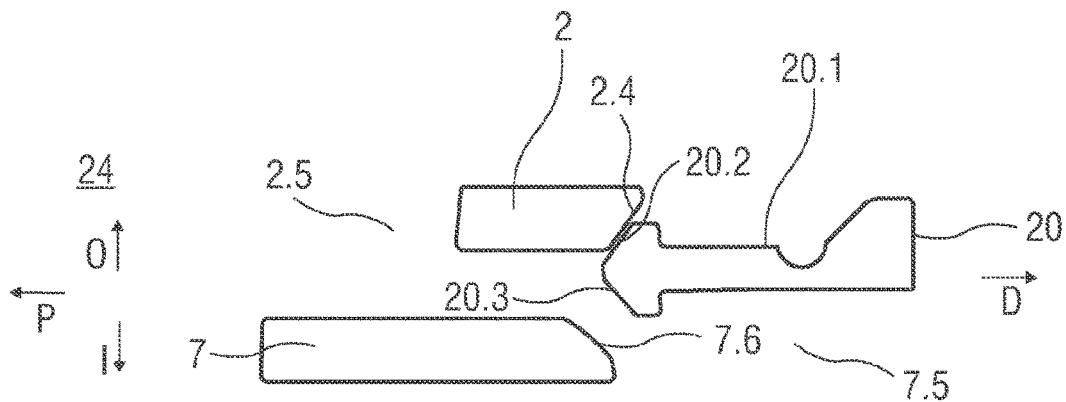
Figure 16C:
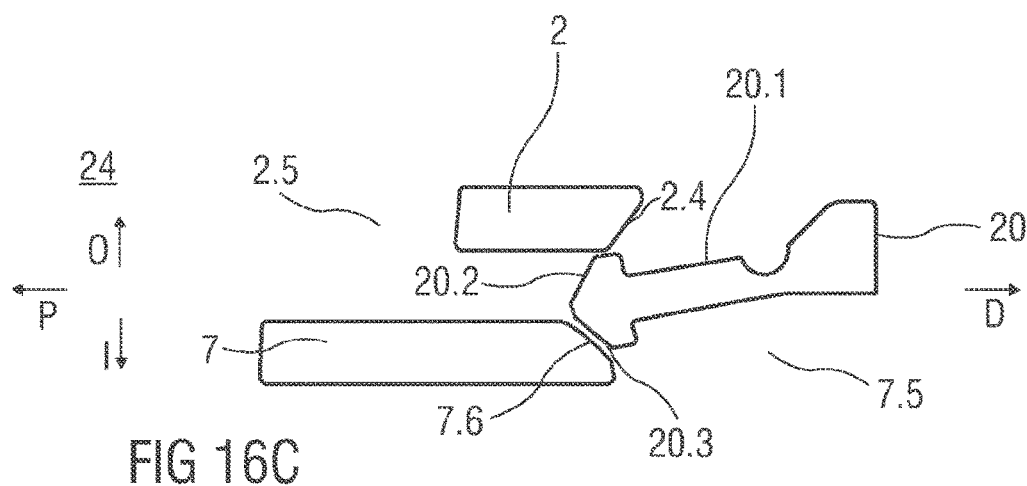

Once the carrier 7 slides far enough in the proximal direction P relative to the first collar 20 the needle insertion control mechanism 24 is switched to a state B as illustrated in FIG. 16B. In FIG. 16B the carrier 7 has been translated in the proximal direction P in such a manner that the arrowhead 20.1 on the first collar 20 is no longer inwardly supported. This may be achieved by a second recess 7.5 in the carrier 7. The arrowhead 20.1 is now deflected in the inward direction I into the second recess 7.5 under load of the control spring 19 arriving at a state C as illustrated in FIG. 16C. The first collar 20 is now decoupled from the chassis 2. Instead, the arrowhead 20.1 couples the first collar 20 to the carrier 7 by an inward ninth ramp 20.3 engaging a distal tenth ramp 7.6 on the carrier 7 at the proximal end of the second recess 7.5. Hence, the control spring 19 continues moving the carrier 7 in the proximal direction P from this point. Whilst the user advances the needle 4 by a proportion of its travel, the control spring 19 takes over insertion before the needle 4 protrudes from the proximal end P. Therefore the user experience is that of pressing a button, rather than manually inserting a needle.

The detent mechanism 18 relies on the user applying a force rather than a displacement. Once the force applied exceeds the force required to switch the detent the user will push the trigger button 13 fully, ensuring that the first collar 20 will always switch. If the user fails to pass the detent, the trigger button 13 returns to its unused state ready for use as illustrated in FIGS. 8A and 8B. This feature avoids the auto-injector 1 arriving in an undefined state.

Figure 9A:
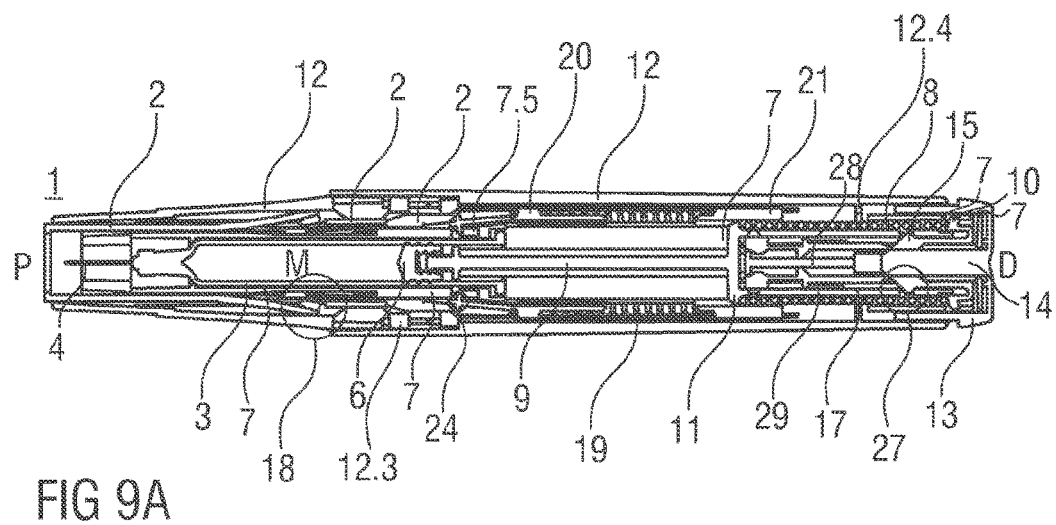
FIG. 9 shows two longitudinal sections of an exemplary embodiment of the auto-injector with a trigger button depressed.
Figure 9B:
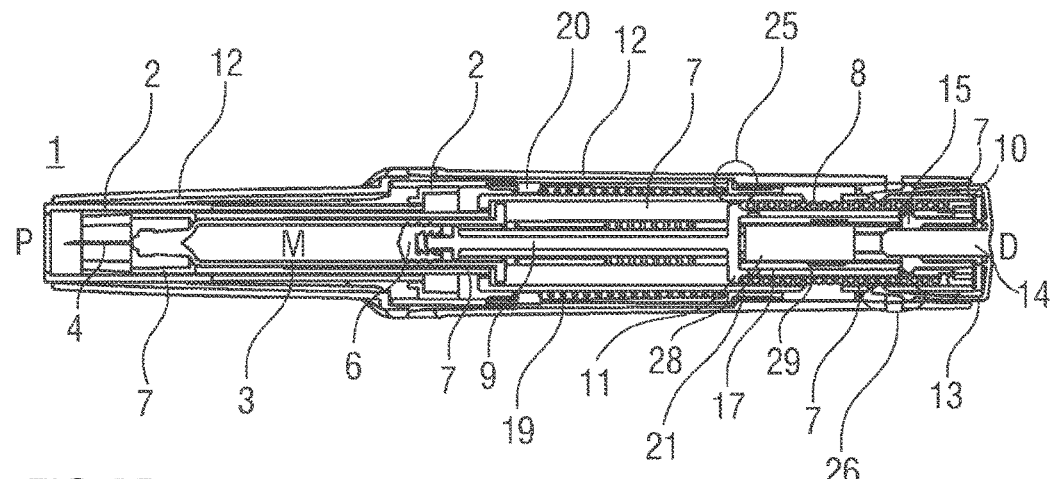

FIGS. 9A and 9B show the auto-injector 1 with the trigger button 13 depressed sufficiently for the control spring 19 to couple on to the carrier 7 and continue moving the carrier 7 in the proximal direction P, but not yet abutting the case 12.

The carrier 7 coupled to the first collar 20 is translated in the proximal direction P driven by the control spring 19. As the syringe 3 is arranged for joint axial translation with the carrier 7, the syringe 3 and needle 4 are also translated resulting in the needle 4 protruding from the proximal end P and being inserted into the injection site. The trigger button 13 returns to its initial position relative to the case 12 and latches back to the case 12 from the carrier 7 as in state A in FIG. 20 A. The carrier 7 translates further in the proximal direction P preventing inward deflection of the proximal beam 13.1 so the outward fourth ramp 13.2 cannot disengage from the first case detent 12.1.

Figure 10A:
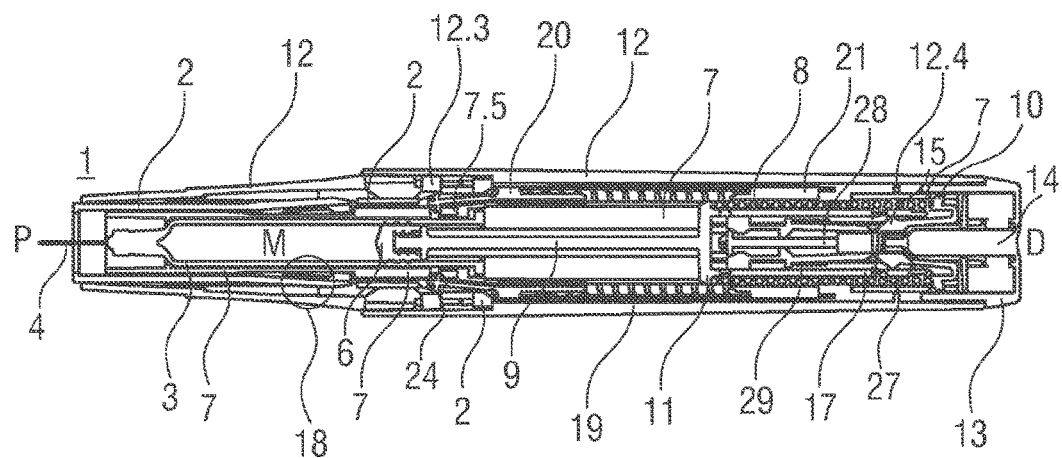
FIG. 10 shows two longitudinal sections of an exemplary embodiment of the auto-injector during needle insertion into the injection site.
Figure 10B:
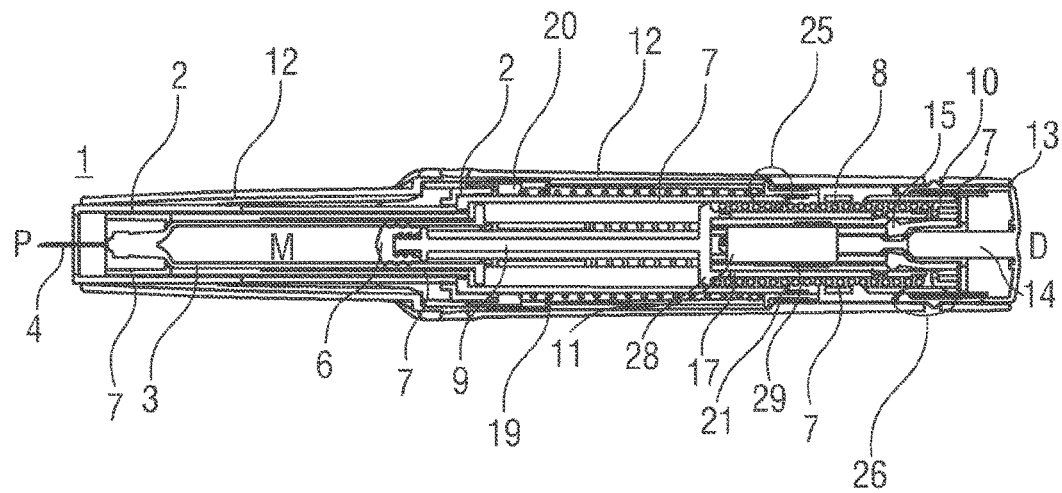
Figure 19B:
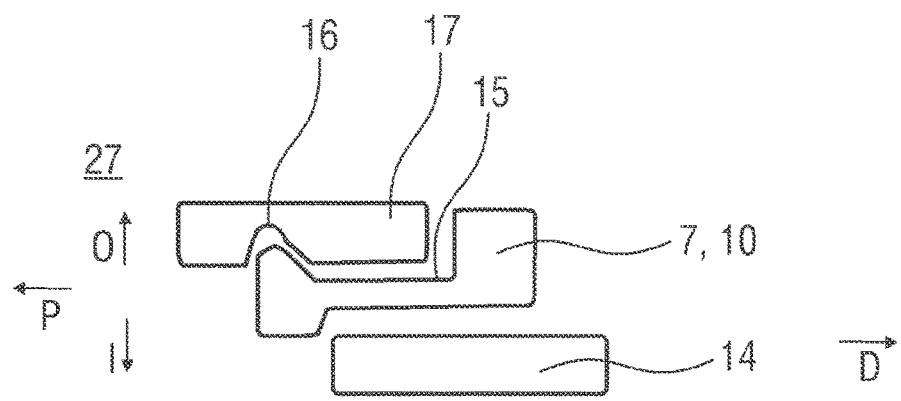
Figure 19C:
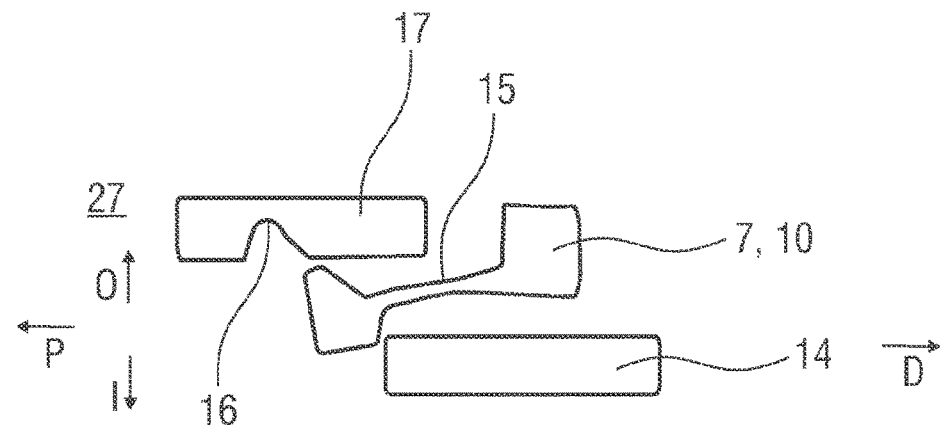

Immediately prior to the needle 4 reaching full insertion depth as illustrated in FIGS. 10A and 10B the peg 14 on the trigger button 13 is completely pulled out from between the resilient arms 15 on the carrier 7. Hence, the plunger release mechanism 27 arrives in a state B shown in FIG. 19B with the resilient arms 15 no longer inwardly supported by the peg 14. Due to the ramped engagement of the resilient arms 15 in the first recess 16 they are deflected in the inward direction I under load of the drive spring 8 illustrated in FIG. 19C. Hence, the plunger 9 is released from the carrier 7 and driven in the proximal direction P by the drive spring 8, ready to inject the medicament M. The force to pull the peg 14 out from between the resilient arms 15 is provided by the control spring 19 while the force required to deflect the resilient arms 15 out of engagement to the plunger 9 is provided by the drive spring 8.

Figure 16D:
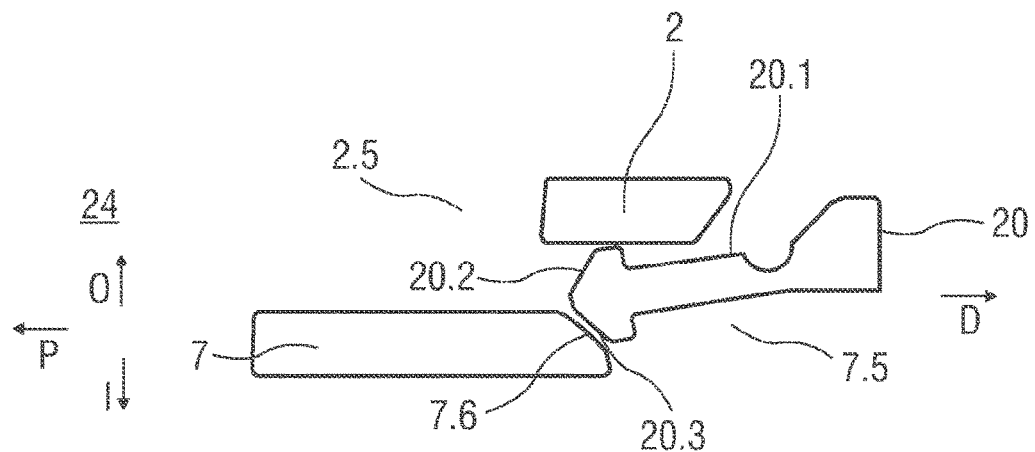

While the plunger 9 moves and closes a gap to the stopper 6, the movement of the carrier 7 in the proximal direction P is completed by the control spring 19 pushing the first collar 20. As the carrier 7 moves with respect to the chassis 2 during needle insertion, the needle insertion mechanism 24 arrives in a state D illustrated in FIG. 16D. The arrowhead 20.1 has moved with the carrier 7 and is still kept inwardly deflected by the chassis 2 thus preventing the first collar 20 from disengaging the carrier 7. The arrowhead 20.1 must be able to deflect in the outward direction O to allow retraction which will be discussed below. In order to allow outward deflection the arrowhead 20.1 travels proximally beyond the part of the chassis 2 shown in FIGS. 16E to 16F next to an aperture 2.5 in the chassis 2. However, as long as the case 12 is being kept pressed against the injection site and not allowed to return in the distal direction D beyond a pre-defined distance under load of the control spring 19, the arrowhead 20.1 will be kept from deflecting in the outward direction O by a sixth rib 12.3 on the case 12 (not illustrated in FIGS. 16A to 16F, see FIGS. 10A to 13A) during about the second half of its motion for needle insertion.

Figure 11A:
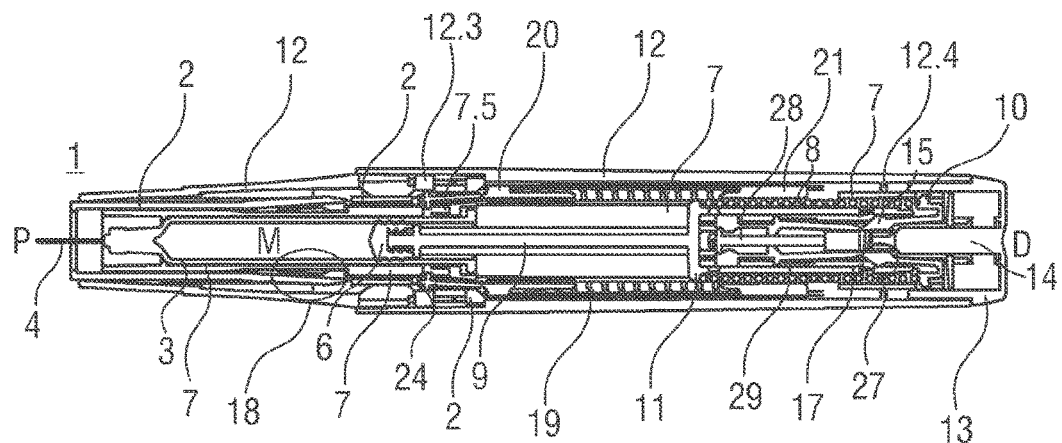
FIG. 11 shows two longitudinal sections of an exemplary embodiment of the auto-injector with the needle fully inserted.
Figure 11B:
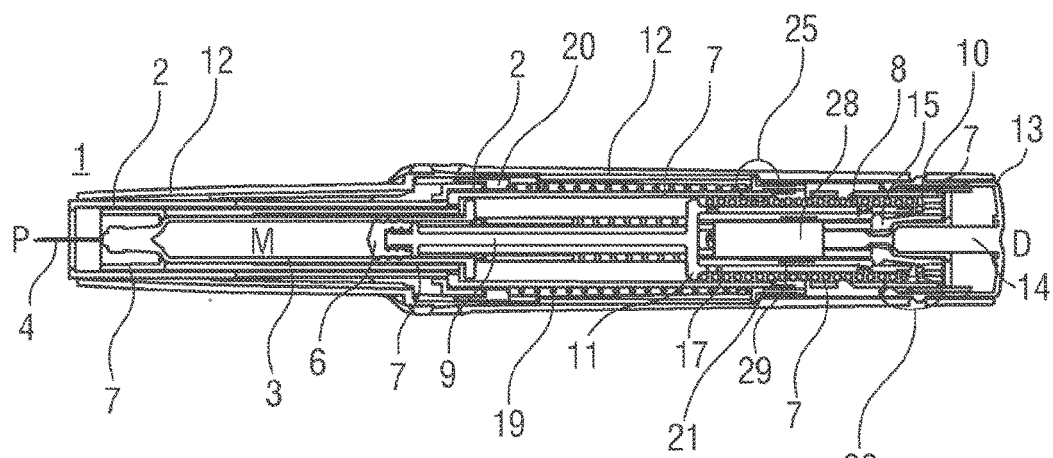

The needle 4 is now fully inserted into the injection site as illustrated in FIGS. 11A and 11B. The time between the trigger button 13 pressed and the needle 4 being fully inserted is very short, however several mechanical operations take place in this time. The needle insertion depth is defined by the carrier 7 relative to the chassis 2 not relative to the case 12, so if the user flinches or fails to hold the auto-injector 1 hard against the skin, only the case 12 will move in the distal direction D while the injection depth remains constant.

As soon as the plunger 9 has closed the gap to the stopper 6 under force of the drive spring 8, the stopper 6 is pushed in the proximal direction P within the syringe 3 displacing the medicament M through the needle 4 into the injection site.

Figure 12A:
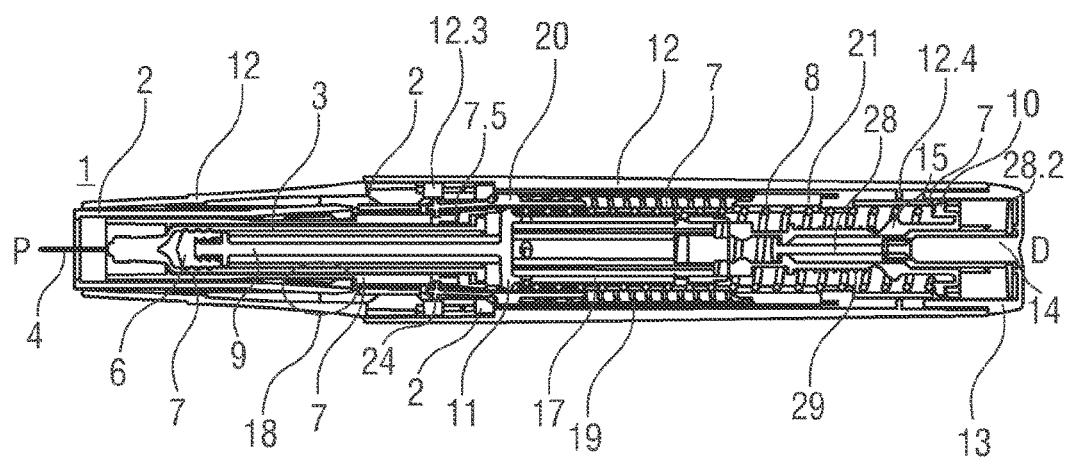
FIG. 12 shows two longitudinal sections of an exemplary embodiment of the auto-injector during injection near the end of dose.
Figure 12B:
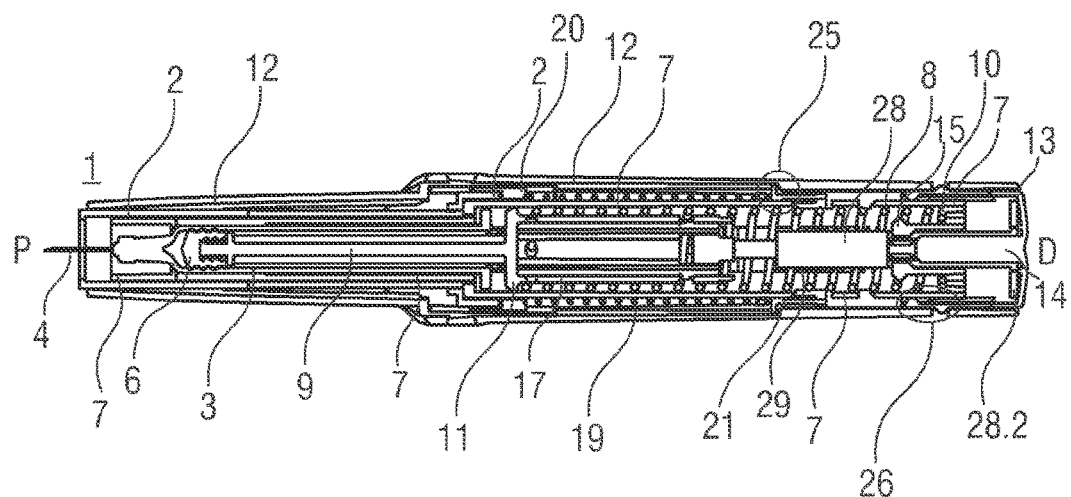

Immediately prior to the end of injection with the stopper 6 having almost bottomed out in the syringe 3 as illustrated in FIGS. 12A and 12B a noise component 28 is released. The noise component 28 comprises an elongate portion 28.1 arranged within the distal plunger sleeve 17 and a distal end plate 28.2 arranged between the carrier end face 10 and an end face of the trigger button 13. Two second resilient arms 30 originate from the distal carrier end face 10 and extend in the proximal direction P. A noise spring 29 is arranged to bias the noise component 28 in the distal direction D relative to the carrier 7 by proximally bearing against a rib on the second resilient arms 30 and distally against the noise component 28 (not illustrated).

Figure 18A:
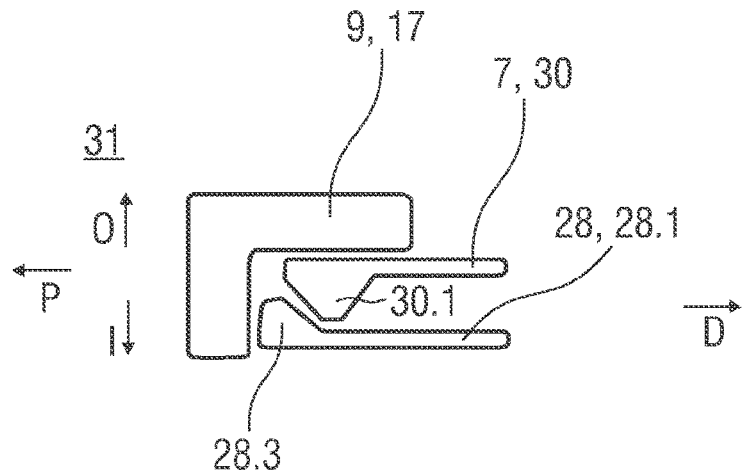
FIG. 18 shows schematic views of an exemplary embodiment of a noise release mechanism for audibly indicating the end of injection in three different states.
Figure 18B:
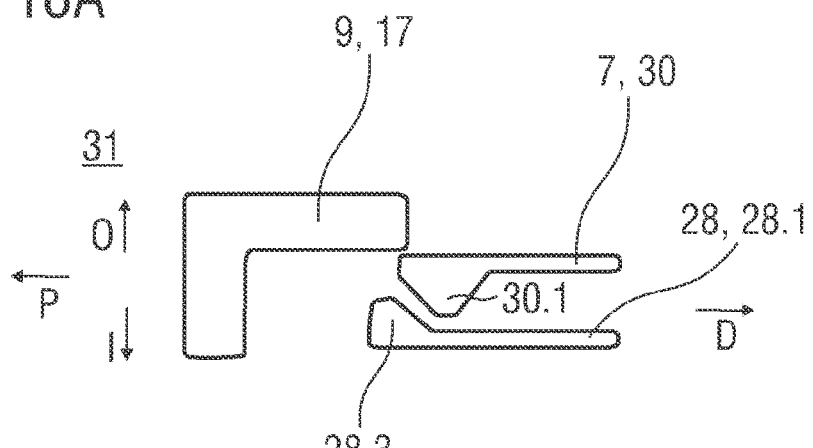
Figure 18C:
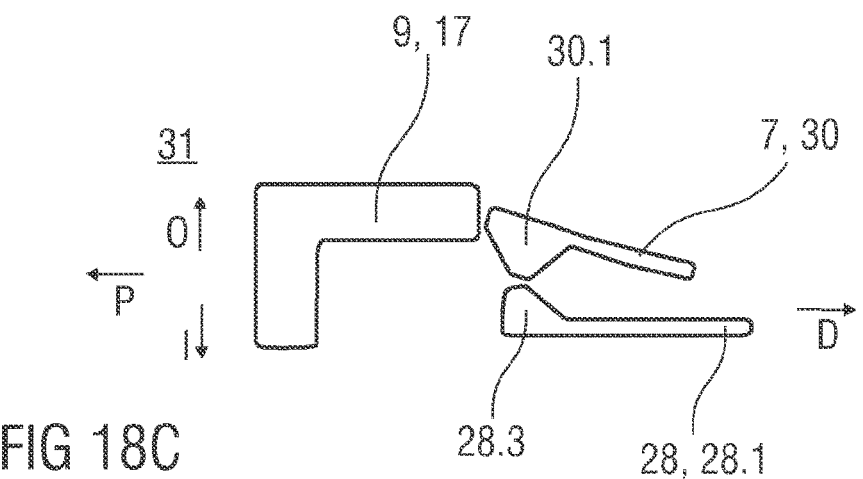

A noise release mechanism 31 for releasing the noise component 28 is schematically illustrated in FIGS. 18A, 18B and 18C. Referring now to FIG. 18A, the noise release mechanism 31 comprises the second resilient arms 30. A ramped inward boss 30.1 is arranged on each second resilient arm 30 which is engaged to a respective outward eleventh ramp 28.3 on the elongate portion 28.1 of the noise component 28 in such a manner that the second resilient arm 30 is deflected in the outward direction O under load of the noise spring 29. In an initial state A of the noise release mechanism 31 the second resilient arms 30 are prevented from being outwardly deflected by outward support of the distal plunger sleeve 17 thus preventing translation of the noise component 28 relative to the carrier 7. The noise release mechanism 31 remains in state A until immediately prior to the end of injection with the stopper 6 having almost bottomed out in the syringe 3 as illustrated in FIGS. 12A and 12B. At this point the plunger 9 has been translated in the proximal direction P relative to the carrier 7 to such an extent that the second resilient arms 30 are no longer supported by the distal plunger sleeve 17. The noise release mechanism 31 has thus arrived in a state B illustrated in FIG. 18B. Due to the ramped engagement between the ramped inward boss 30.1 and the outward eleventh ramp 28.3 the second resilient arm 30 is outwardly deflected under load of the noise spring 29 thus disengaging the noise component 28 from the carrier 7 and allowing the noise component 28 to move in the distal direction D driven by the noise spring 29 in a state C illustrated in FIG. 18C. Hence, the noise component 28 is accelerated in the distal direction D and the distal end plate 28.2 impacts on the inside of the trigger button 13 producing audible and tactile feedback to the user that the injection is about finished.

Figure 13A:
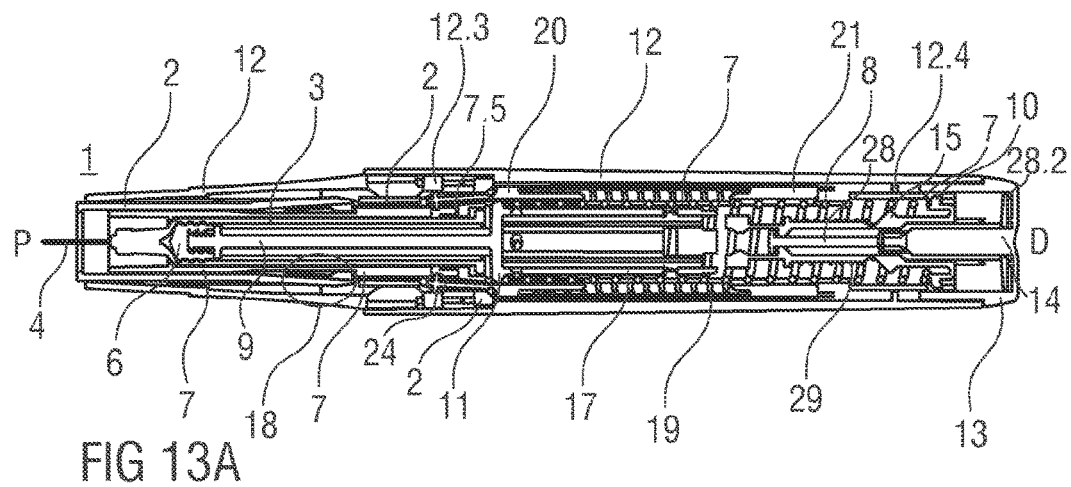
FIG. 13 shows two longitudinal sections of an exemplary embodiment of the auto-injector at the end of dose.
Figure 13B:
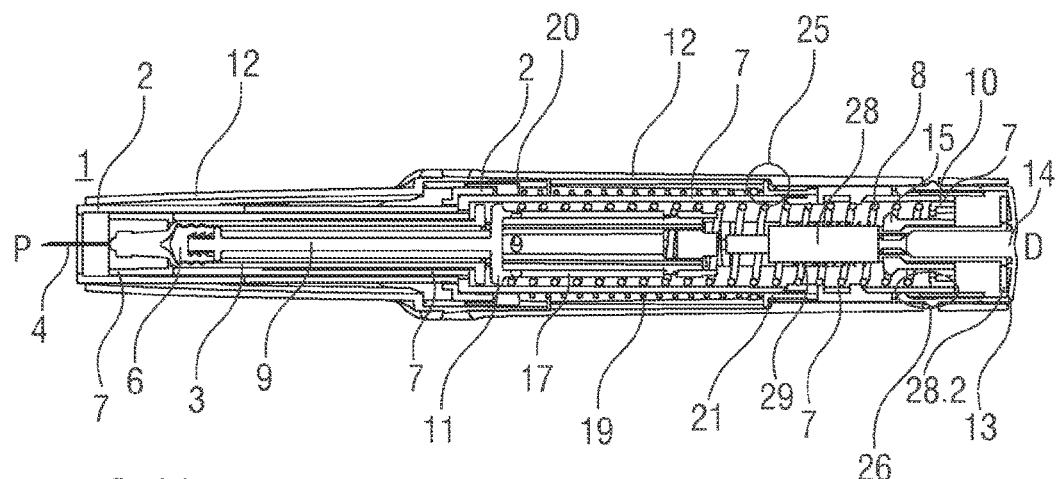

FIGS. 13A and 13B show the auto-injector 1 with the stopper 6 having entirely bottomed out in the syringe 3.

Figure 14A:
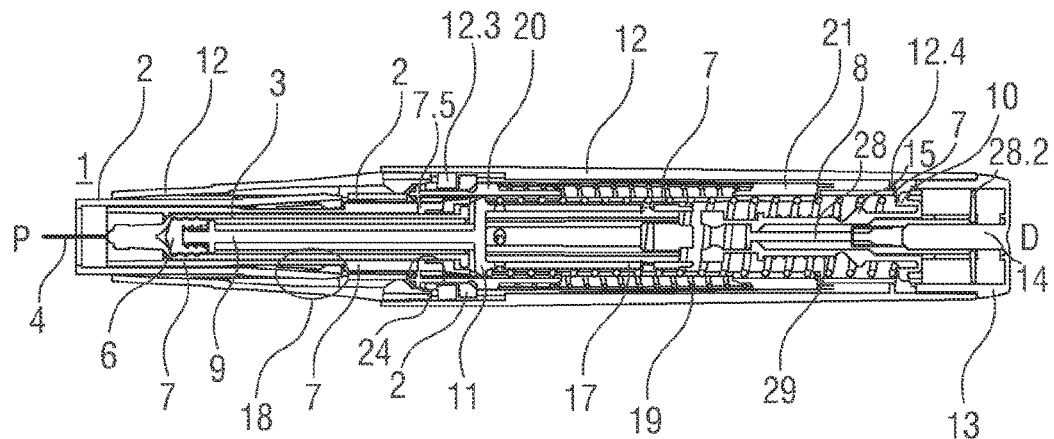
FIG. 14 shows two longitudinal sections of an exemplary embodiment of the auto-injector removed from the injection site.
Figure 14B:
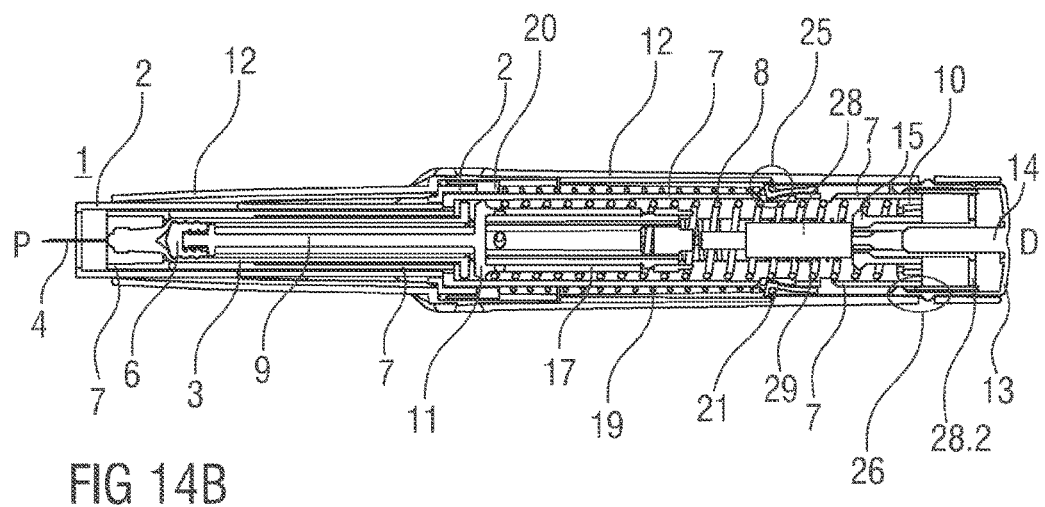

As mentioned above the user is able to let the case 12 move by a few millimeters in the distal direction D under the force of the control spring 19 without affecting the position of the needle 4 as long as that motion is below a predefined distance. If the user wishes to end the injection, at any time, they must allow the case 12 to move in the distal direction D beyond that distance. FIGS. 14A and 14B show the auto-injector 1 lifted from the injection site with the case 12 moved all the way in the distal direction D so that the chassis 2 protrudes from the proximal end of the case 12. As the case 12 is moved the first collar 20 releases the carrier 7 and then the second collar 21 releases from the case 12 and pulls the carrier 7 in the distal direction D. Retraction may fail if both collars 20, 21 are attached to the carrier 7 at the same time. This is overcome by separating the switching of the collars 20, 21 by an axial displacement of the case 12.

Figure 16E:
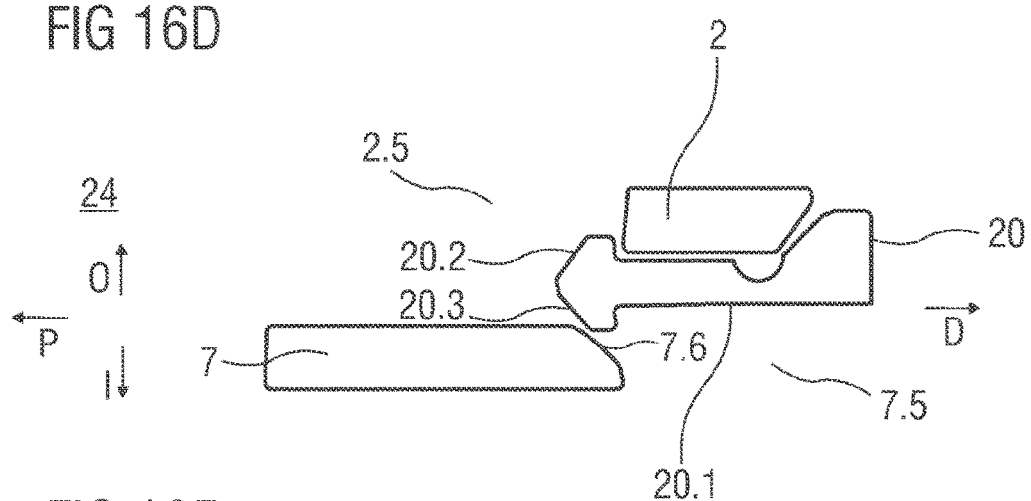
Figure 16F:
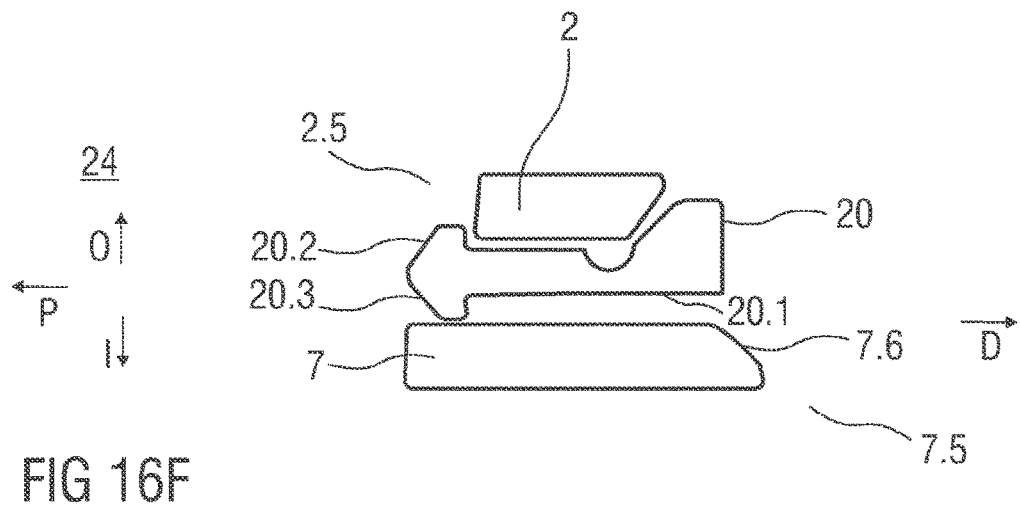

The switching of the first collar 20 is illustrated in FIGS. 16E and F. In FIG. 16E the case 12 has been allowed to move in the distal direction D under load of the control spring 19 during removal of the auto-injector 1 from the injection site. The sixth rib 12.3 (not illustrated, see FIG. 14A) is removed from outwardly behind the arrowhead 20.1. The first collar 20 is still being pushed in the proximal direction P by the control spring 19. Due to the engagement of the inward ninth ramp 20.3 on the arrowhead 20.1 with the distal tenth ramp 7.6 on the carrier 7 the arrowhead 20.1 is deflected in the outward direction O into the aperture 2.5 of the chassis 2 (illustrated in FIGS. 16A to 16F), the needle insertion control mechanism 24 arriving in a state E as illustrated in FIG. 16E, decoupling the first collar 20 from the carrier 7 and latching it to the chassis 2.

Figure 17B:
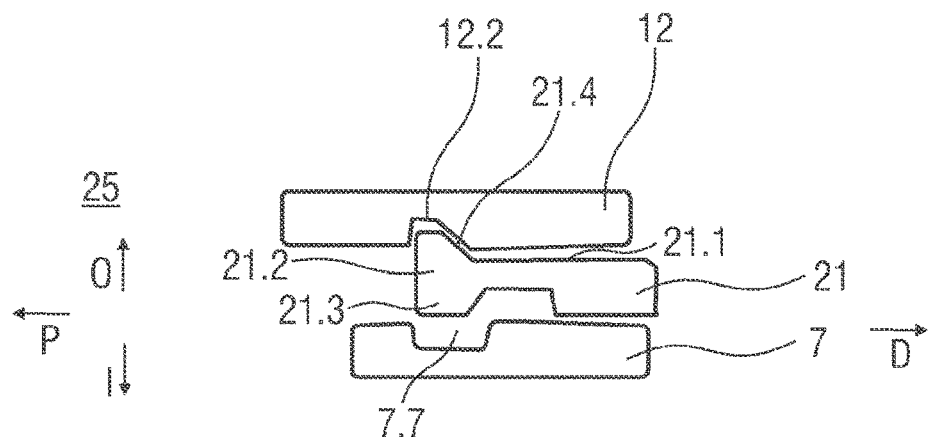
Figure 17C:
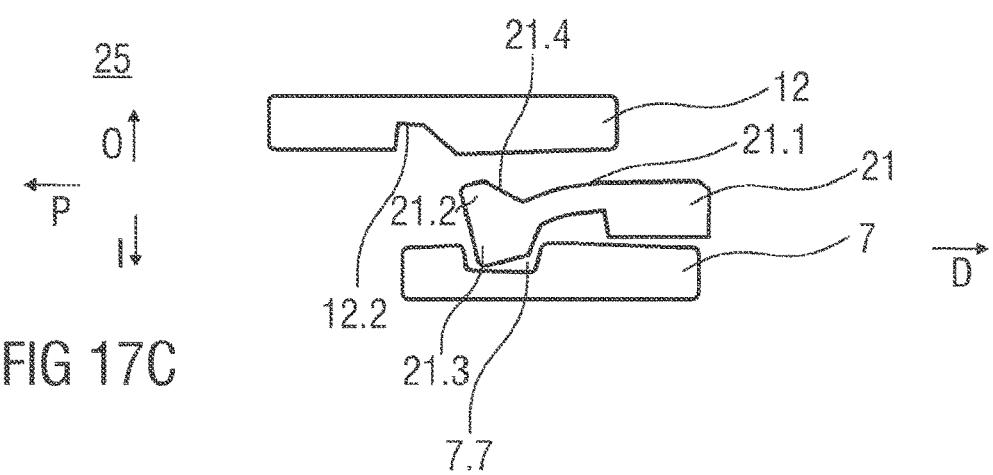

As the case 12 is moving further in the distal direction D on removal from the injection site the syringe retraction control mechanism 25 switches from its state A (cf. FIG. 17A) into a state B illustrated in FIG. 17B. The case 12 and the second collar 21 locked to the case 12 move together in the distal direction D while the carrier 7 is held in place by the detent mechanism 18 in its state D as described above (cf. FIGS. 4A, B). Due to this motion the inward boss 21.3 on the second beam head 21.2 of the proximal beam 21.1 on the second collar 21 no longer inwardly abuts the carrier 7. Instead the inward boss 21.3 is deflected in the inward direction I into a third recess 7.7 in the carrier 7 due to the ramped engagement of the second beam head 21.1 to the ramped second case detent 12.2 under load of the control spring 19. The syringe retraction control mechanism 25 thus arrives in a state C as illustrated in FIG. 17C with the second collar 21 decoupled from the case 12 and coupled to the carrier 7. The detent mechanism 18 applies a small retarding force to the movement of the carrier 7 before the syringe retraction control mechanism 25 switches to state C as there is a small sliding force, applied by the second collar 21, pulling the carrier 7 in the distal direction D on translation of the case 12 in the distal direction D when the needle insertion control mechanism 24 has already been switched into state E. If the carrier 7 moves too far in the distal direction D before the second collar 21 switches, the case 12 runs out of travel before the inward boss 21.3 can deflect into the third recess 7.7 preventing retraction.

Starting from the position D of the detent mechanism 18 (cf. FIGS. 4A, B) the carrier 7 and hence the ramp member 7.1 are translated in the distal direction D under load of the control spring 19. Hence, the detent beam 2.1 is deflected in the tangential direction T. This applies the small retarding force to the movement of the carrier 7 required for ensuring the switching of the second collar 21 to the carrier 7.

The control spring 19 is grounded at its proximal end in the case by the first collar 20 being abutted against the chassis 2. The distal end of the control spring 19 moves the second collar 21 in the distal direction D taking with it the carrier 7 and hence the syringe 3 with the needle 4 overcoming the detent mechanism 18 in a state E as illustrated in FIGS. 5A, B. Note that the needle 4 is retracted out of the skin by the auto-injector 1 as soon as the user allows the case 12 to translate sufficiently far as opposed to auto-injectors with needle shields which require the user to remove the auto-injector from the injection site thereby themselves pulling the needle out of the skin for allowing the needle shield to advance.

As the movement allowed of the noise component 28 is limited relative to the carrier 7 it is no longer in contact with the trigger button 13 which has moved in the distal direction D with the case 12 on removal from the injection site. When the retraction begins the noise spring 29 does not provide any retarding force. Once the noise component 28 hits the trigger button 13 again on retraction of the carrier 7 the noise spring 29 must be recompressed, reducing the force driving the final part of retraction. In order to ensure a reliable retraction despite this reducing force the control spring 19 must be appropriately dimensioned.

Figure 15A:
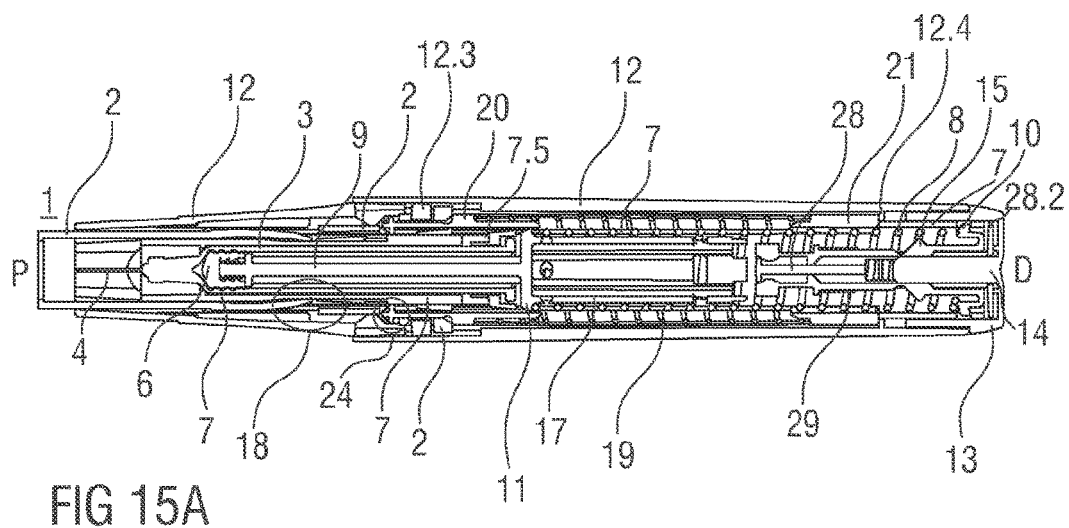
FIG. 15 shows two longitudinal sections of an exemplary embodiment of the auto-injector with the needle retracted into a needle safe position.
Figure 15B:
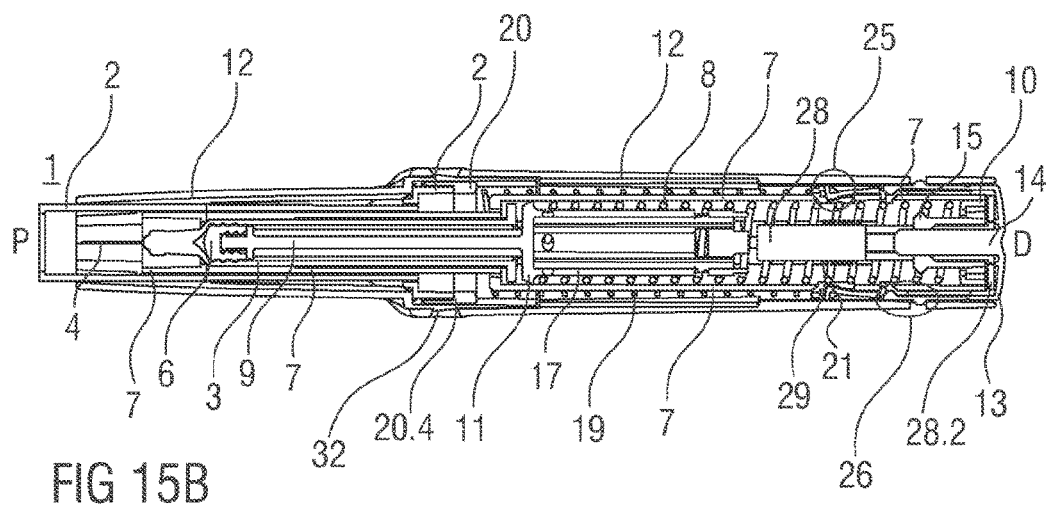

The retraction ends when the distal collar 21 meets a first back stop 12.4 on the case 12 as in FIGS. 15A and 15B. The arrowhead 20.1 on the first collar 20 is inwardly supported by the carrier 7 in a state F illustrated in FIG. 16F and thus prevented from deflecting in the inward direction I. The outward sixth ramp 20.2 of the arrowhead 20.1 is engaged behind the sixth rib 12.3 on the case 12 preventing the case 12 from being pushed in the proximal direction P again. A clearance may be provided between the arrowhead 20.1 and the sixth rib 12.3 to allow for tolerances.

The detent mechanism 18 returns to state A as in FIGS. 1A, B locking the carrier 7 in position relative to the chassis 2 as it did initially, however it cannot be unlocked now as the case 12 cannot move relative to the chassis 2.

A tab 20.4 on the first collar 20 is now visible through an indicator window 32 in the case 12—indicating the auto-injector 1 has been used.

Figure 21:
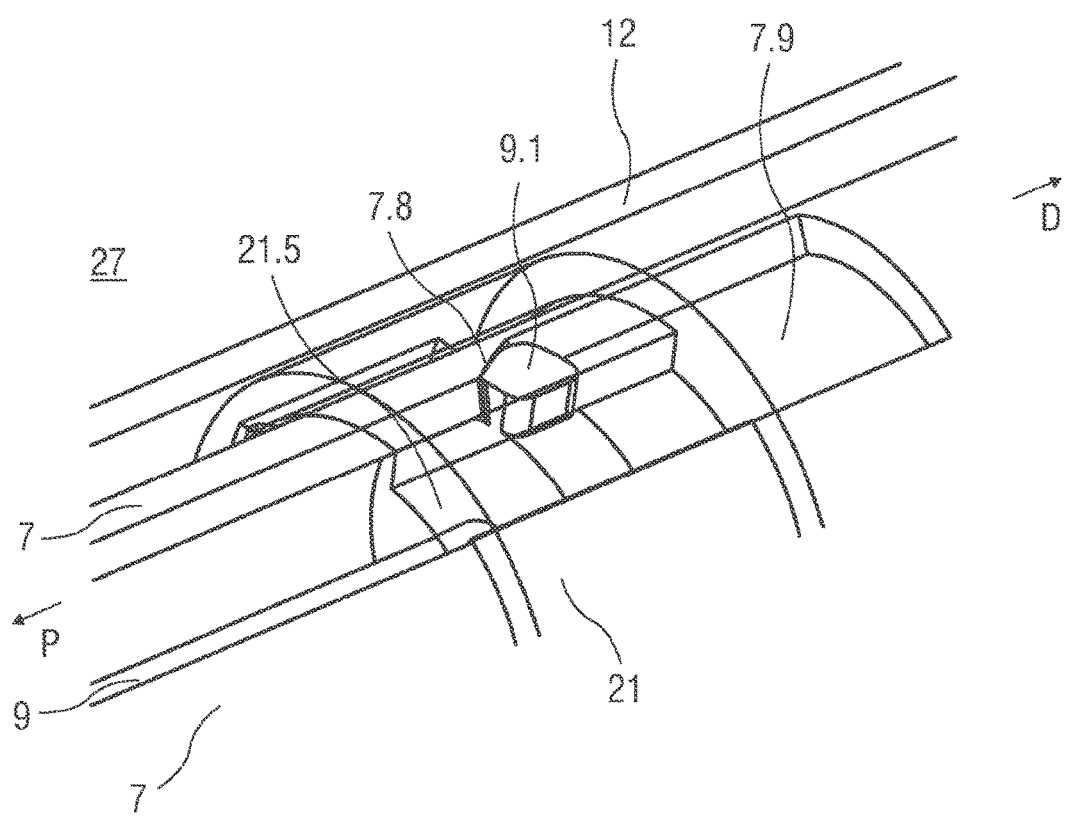
FIG. 21 is an isometric view of an alternative embodiment of the plunger release mechanism.

FIG. 21 is an isometric view of an alternative embodiment of the plunger release mechanism 27. The plunger release mechanism 27 prevents movement of the plunger 9 in the proximal direction P relative to the carrier 7 until the carrier 7 is moved in the proximal direction P for needle insertion. As opposed to the plunger release mechanism 27 of FIG. 19, where relative movement of the carrier 7 and trigger button 13 are used to trigger the release of the plunger 9, the alternative embodiment of FIG. 21 releases the plunger 9 by movement of the carrier 7 relative to the second collar 21. FIG. 21 illustrates the plunger release mechanism 27 prior to plunger release. The second collar 21 is shown transparent to improve clarity. The plunger 9 is being pushed in the proximal direction P by the drive spring 8. In order for the plunger 9 to advance, it must rotate around a twelfth ramp 7.8 on the carrier 7. A ramp member 9.1 on the plunger 9 is arranged to engage this twelfth ramp 7.8. Rotation of the ramp member 9.1 is blocked by an inward longitudinal rib 21.5 on the second collar 21 splined in a longitudinal aperture 7.9 in the carrier 7. The case 12 and the second collar 21 remain in the same position, i.e. coupled to each other for joint axial translation. On depression of the trigger button 13 the carrier 13 and the plunger 9 being part of the drive sub-assembly are moved in the proximal direction P, first by the user pressing the trigger button 13 and then by the control spring 19 taking over via the first collar 20 as described above. Once the carrier 7 moves sufficiently far in the proximal direction P relative to the second collar 21 the ramp member 9.1 on the collar 9 comes clear of the longitudinal rib 21.5 on the second collar 21 and can rotate past the proximal end of the longitudinal rib 21.5 due to its ramped engagement to the twelfth ramp 7.8 under load of the drive spring 8. Hence, the drive spring 8 advances the plunger 9 in the proximal direction P for injecting the medicament M.

Figure 22:
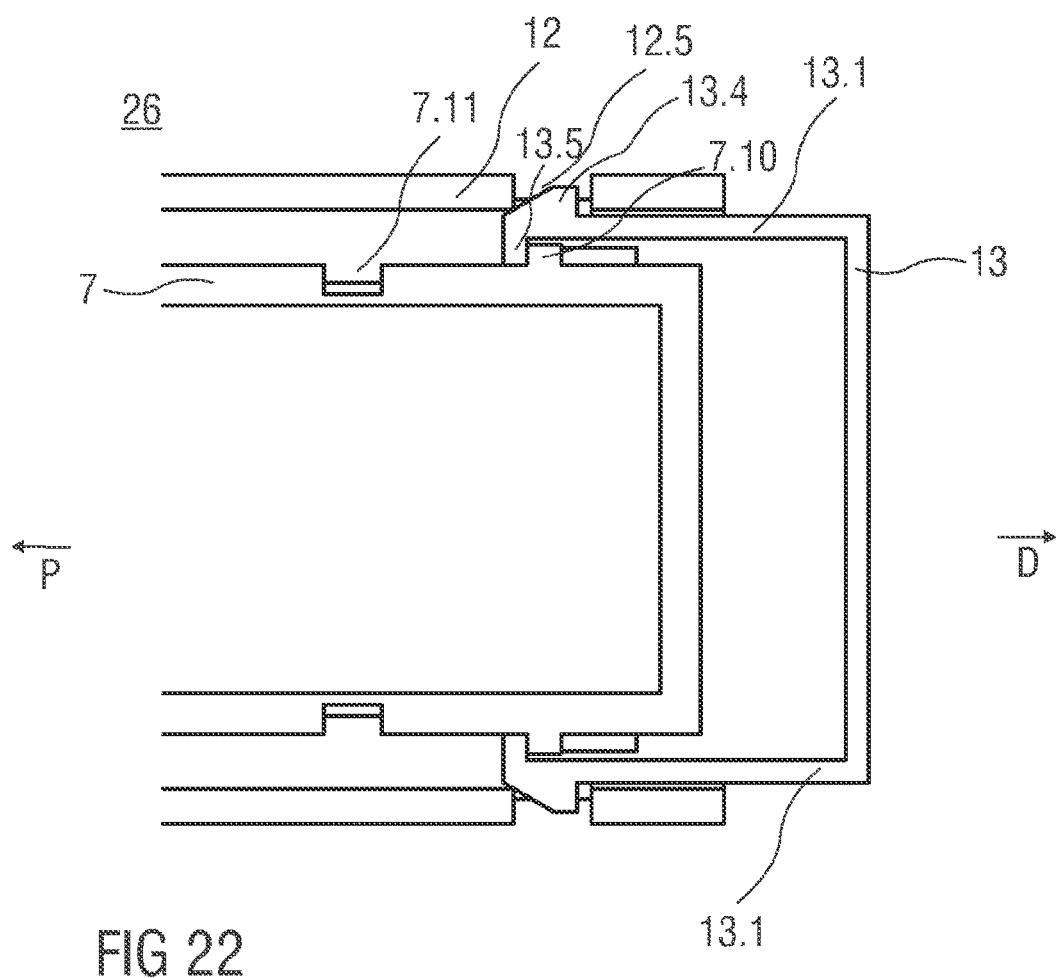
FIG. 22 is a longitudinal section of an alternative embodiment of the button release mechanism.

FIG. 22 is a longitudinal section of an alternative embodiment of the button release mechanism 26. Other than the button release mechanism 26 of FIG. 20 which gives the appearance of a revealing trigger button 13 on skin contact by switching the ground of the trigger button 13 between the carrier 7 and the case 12, the button release mechanism 26 of FIG. 22 starts with the trigger button 13 locked but protruding from the distal end of the case 12. Once the carrier 7 has moved in the distal direction D on skin contact of the chassis 2, it is possible to depress the trigger button 13 and activate the auto-injector 1. This ensures a sequenced operation.

In the embodiment of FIG. 22 the trigger button 13 has two proximal beams 13.1, each of them having a ramped outward boss 13.4. In the initial state shown in FIG. 22 the ramped outward bosses 13.4 are engaged in respective fourth recesses 12.5 in the case 12. Disengaging the ramped outward bosses 13.4 from the fourth recesses 12.5 is prevented by the carrier 7 inwardly supporting the proximal beams 13.1 in a manner to keep the proximal beams 13.1 from deflecting inwardly. Inward protrusions 13.5 on the proximal beams 13.1 abut against a second rib 7.10 on the carrier 7 in a manner preventing the carrier 7 from moving further in the proximal direction P in the initial state. Once the carrier 7 has moved in the distal direction D on skin contact of the chassis 2 a first window 7.11 in the carrier 7 is moved behind the inward protrusion 13.5 so as to allow the proximal beams 13.1 to be inwardly deflected due to their ramped engagement in the fourth recesses 12.5 on depression of the trigger button 13. The proximal beams 13.1 are now outwardly supported by the case 12 and remain engaged to the carrier 7 even on retraction of the needle 4. The trigger button 13 does therefore not return to its initial position, indicating that the auto-injector 1 has been used.

The button release mechanism 26 illustrated in FIG. 22 may preferably be combined with the plunger release mechanism 27 illustrated in FIG. 21.

Figure 23:
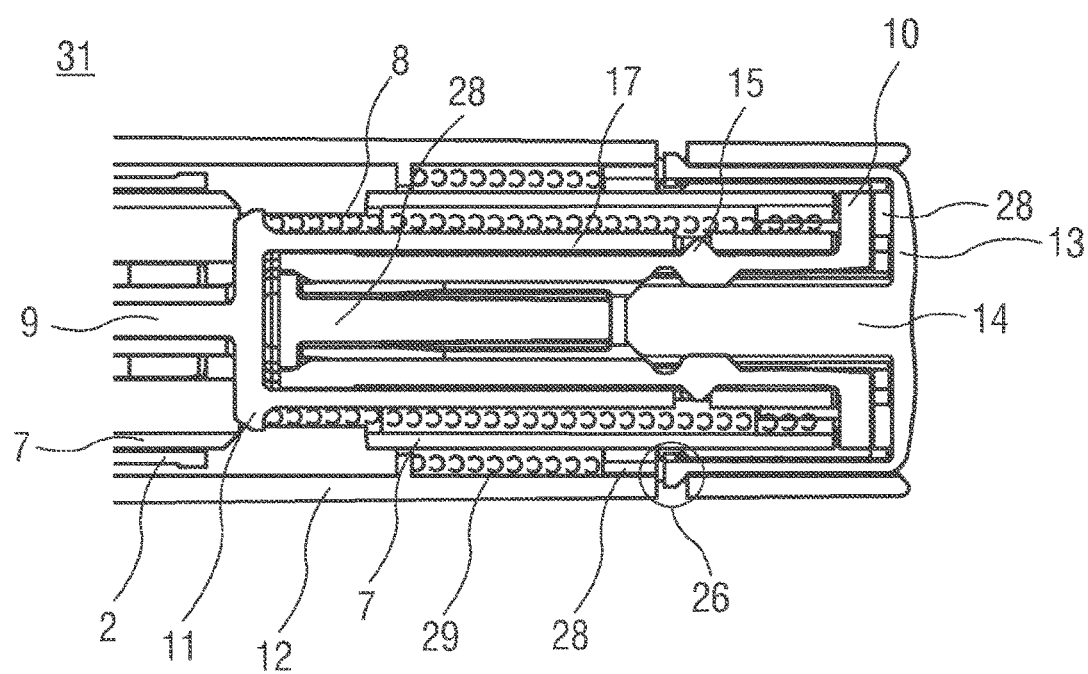
FIG. 23 is a longitudinal section of an alternative embodiment of the noise release mechanism.

FIG. 23 is a longitudinal section of an alternative embodiment of the noise release mechanism 31. As opposed to the noise release mechanism 31 of FIG. 18 where the noise spring 29 acts between the carrier 7 and the noise component 28, in the embodiment illustrated in FIG. 23 the noise spring 29 acts between the case 12 and the noise component 28. During needle insertion the noise spring 29 is compressed as the noise component 28 moves with the carrier 7 relative to the case 12. When the noise component 28 is released by the plunger 9 shortly before the end of dose, the noise component 28 moves in the distal direction D and impacts the trigger button 13. Other than in FIG. 18 the noise spring 29 is not being recompressed during needle retraction since it is grounded in the case 12 not in the carrier 7.

Figure 24A:
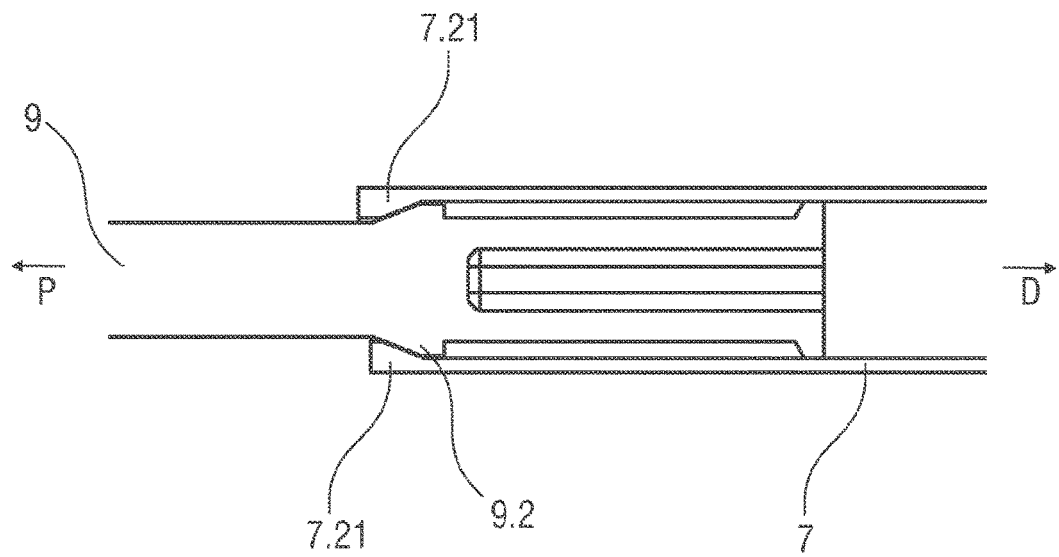
FIG. 24 shows longitudinal sections of a third embodiment of the noise release mechanism.
Figure 24B:
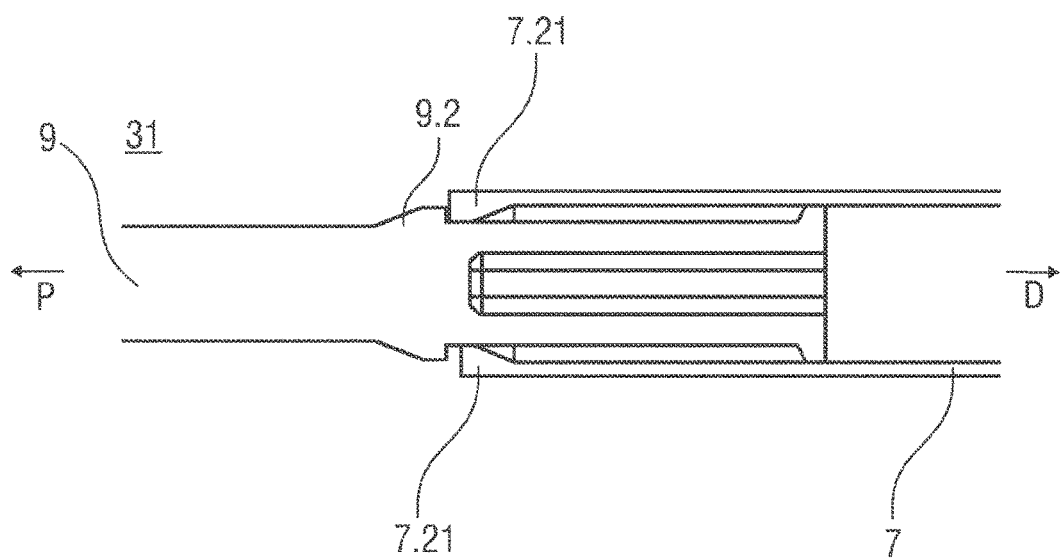

FIGS. 24A and 24B show a longitudinal section of a third embodiment of the noise release mechanism 31. This embodiment works without the need for a dedicated noise spring. The plunger 9 comprises a proximally ramped rib 9.2 arranged to splay two seventh clips 7.21 on the carrier 7 immediately prior to the end of dose. When the proximally ramped rib 9.2 has travelled past the seventh clips 7.21 they snap back and impact the plunger 9 generating a sound. The tubular shape of the carrier 7 helps to transmit the sound. FIG. 24A shows the noise release mechanism 31 before release. FIG. 24B shows the noise release mechanism 31 after release. Proximal faces of the seventh clips 7.21 on the carrier 7 are axially offset to facilitate assembly by lifting the seventh clips 7.21 over the distal side of the proximally ramped rib 9.2 one by one.

Figure 25A:
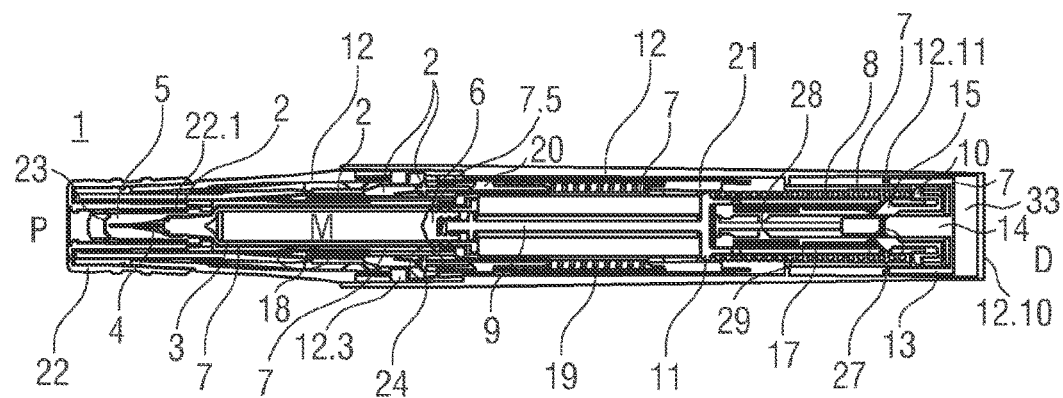
FIG. 25 is another embodiment of the auto-injector having a wrap-over sleeve trigger instead of a trigger button.
Figure 25B:
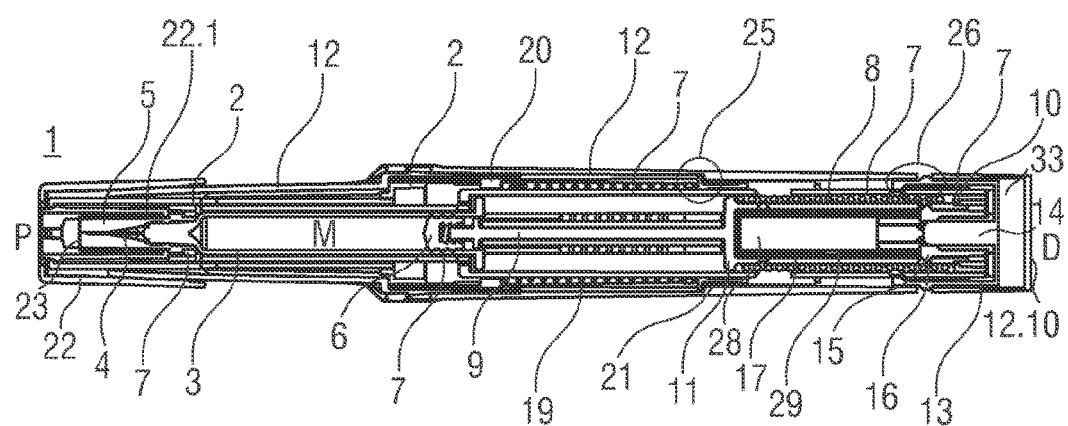

FIGS. 25A and 25B show longitudinal sections of another embodiment of the auto-injector 1 in different section planes, the different section planes approximately 90° rotated to each other, wherein the auto-injector 1 is in an initial state prior to starting an injection. The auto-injector 1 is essentially identical to the one described in FIGS. 6 to 20. However, other than the auto-injector of FIGS. 6 to 20 the auto-injector 1 of this embodiment has a wrap-over sleeve trigger instead of a trigger button.

The wrap-over sleeve trigger 12 is the same component as the case 12 which has a closed distal end face 12.10 other than the one in FIGS. 6 to 20. An internal trigger button 13 is arranged at the distal end inside the sleeve trigger 12. Other than in FIGS. 6 to 20 the trigger button 13 is not visible nor does it protrude from the case 12 in any state. In the initial state a clearance 33 is provided between the distal end face 12.10 of the sleeve trigger 12 and the internal trigger button 13 allowing for some travel of the sleeve trigger 12 without interfering with the trigger button 13.

As the auto-injector 1 does not differ from the auto-injector of FIGS. 6 to 20 in other respects it is essentially operated in the same way with the following exceptions:

As the chassis 2 is placed against the injection site the sleeve trigger 12 translates in the proximal direction P relative to the chassis 2 into the advanced position in a first phase of sleeve travel removing the clearance 33 between the distal end face 12.10 of the sleeve trigger 12 and the internal trigger button 13. As in the embodiment of FIGS. 6 to 20 this motion unlocks the detent mechanism 18 and the trigger button 13. As the user continues to depress the sleeve trigger 12 in a second phase of sleeve travel thereby further advancing it in the proximal direction P the distal end face 12.10 hits the internal trigger button 13 thereby depressing it until the first collar 20 is released from the chassis 2 and the control spring force is coupled on to the carrier 7. The carrier 7 then advances until the internal trigger button 13 stops on another rib in the case 12 and the plunger release mechanism 27 is released (note the peg 14 is shorter in this embodiment.

From a user perspective, the detent mechanism 18 is arranged to provide a resistive force when the user reaches the second phase of sleeve travel. Internally, there is no difference to the embodiment of FIGS. 6 to 20 at this point.

Needle insertion is triggered by the user fully advancing the sleeve trigger 12 in the second phase of sleeve travel thereby fully depressing the internal trigger button 13 and overcoming the detent mechanism as in the embodiment of FIGS. 6 to 20.

Figure 20C:
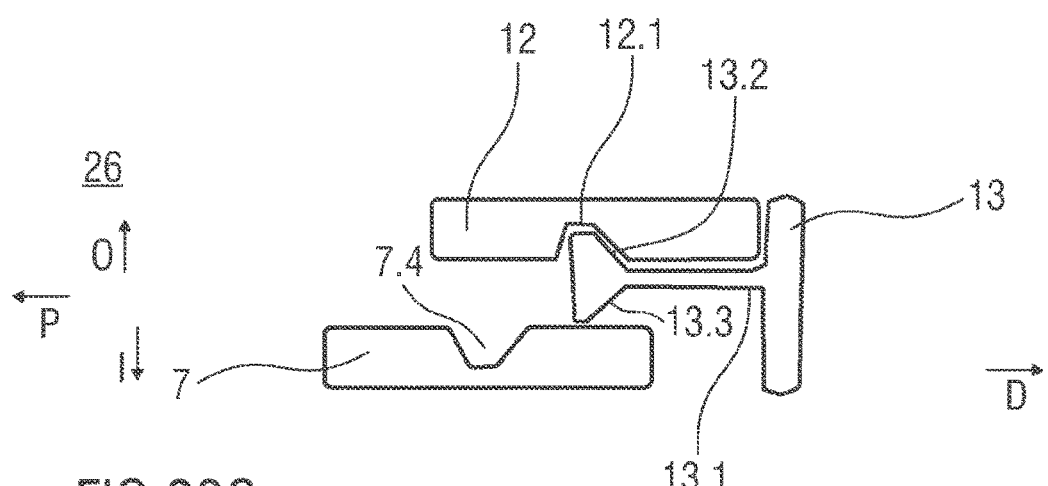

As the control spring 19 takes over on button depression fully advancing the carrier 7 for needle insertion the internal trigger button 13 bottoms out on an internal fifth rib 12.11 in the sleeve trigger 12 and the internal trigger button 13 switches back to being locked to the sleeve trigger 12 as in FIG. 20C.

The embodiment of FIGS. 25A and 25B may also be combined with the alternative features illustrated in FIGS. 21 to 24.

It goes without saying that in all ramped engagements between two components described in the above embodiments there may be just one ramp on one or the other component or there may be ramps on both components without significantly influencing the effect of the ramped engagement.

The invention claimed is:

1. An auto-injector comprising
a syringe carrier adapted to contain at least a majority of a syringe, the syringe carrier having a ramp member with a first ramp and a second ramp, wherein the ramp member defines a longitudinal axis; and
a chassis including a resilient beam having a beam head adapted to engage the ramp member, wherein the carrier is slidably arranged in the chassis,
wherein the first ramp is adapted to deflect the beam head in a radial direction relative to the chassis, when the syringe carrier moves in a first direction relative to the chassis, and the second ramp is adapted to deflect the beam head in a tangential direction relative to the chassis, wherein the radial direction is perpendicular to the longitudinal axis, and wherein the tangential direction is perpendicular to the longitudinal axis and the radial direction
wherein the beam head is configured to be deflected by the first ramp when the syringe carrier moves in the first direction relative to the chassis, and the beam head is configured to be deflected by the second ramp when the syringe carrier moves in a second direction relative to the chassis, wherein the first direction is opposite the second direction.

2. The auto-injector according to claim 1, further comprising
a case including a first rib and a resilient element, wherein the first rib and the resilient element are adapted to engage the beam head.

3. The auto-injector according to claim 2, wherein the beam head includes a first beam head adapted to engage the ramp member and a second beam head adapted to engage the case.

4. The auto-injector according to claim 3, wherein the first beam head has a contoured engagement surface.

5. The auto-injector according to claim 2, wherein, in a first state, the beam head is configured to abut the first rib and the first ramp to prevent movement of the syringe carrier relative to the chassis.

6. The auto-injector according to claim 5, wherein, in a second state, the beam head is configured to be deflected radially by the first ramp and causes the resilient element to deflect radially.

7. The auto-injector according to claim 6, wherein, in a third state, the beam head is configured to disengage the first ramp and the syringe carrier is translatable relative to the chassis.

8. The auto-injector according to claim 7, wherein, in the third state, the beam head is configured to remain in contact with a portion of the ramp member, the portion excluding the first ramp.

9. The auto-injector according to claim 8, wherein, in a fourth state, the beam head is configured to be in a non-deflected position distal of the second ramp.

10. The auto-injector according to claim 9, wherein the beam head is configured to reach the fourth state when the syringe carrier translates in a first direction relative to the chassis a predetermined distance at least equal to a length of the ramp member.

11. The auto-injector according to claim 10, wherein, in a fifth state, the beam head is configured to be deflected tangentially by the second ramp and the syringe carrier is translatable relative to the chassis.

12. The auto-injector according to claim 11, wherein the beam head is configured to reach the fifth state when the syringe carrier translates in the second direction relative to the chassis until the beam head abuts the second ramp.

13. The auto-injector according to claim 1, wherein the first ramp is formed on a proximal portion of the ramp member and the second ramp is formed on a distal portion of the ramp member.

14. The auto-injector according to claim 1, wherein a first plane of the first ramp intersects a second plane of the second ramp at a non-perpendicular angle.

* * * * *